US011376229B2

(12) United States Patent
Friese et al.

(10) Patent No.: US 11,376,229 B2
(45) Date of Patent: Jul. 5, 2022

(54) METHOD OF TREATING OR PREVENTING NEURODEGENERATION

(71) Applicant: Reprise Pharmaceuticals, Inc., New York, NY (US)

(72) Inventors: Manuel Friese, Hamburg (DE); Benjamin Schattling, Hamburg (DE); Karin Steinbach, Geneva (CH); Marc Freichel, Saarlouis (DE); Veit Flockerzi, Blieskastel (DE); Rudi Vennekens, Herent (BE); Doron Merkler, Chancy (CH)

(73) Assignee: REPRISE PHARMACEUTICALS, INC., New York, NY (US)

( * ) Notice: Subject to any disclaimer, the term of this patent is extended or adjusted under 35 U.S.C. 154(b) by 0 days.

(21) Appl. No.: 17/108,649

(22) Filed: Dec. 1, 2020

(65) Prior Publication Data
US 2021/0077436 A1 Mar. 18, 2021

Related U.S. Application Data

(63) Continuation of application No. 16/534,243, filed on Aug. 7, 2019, which is a continuation of application No. 14/369,624, filed as application No. PCT/EP2012/076773 on Dec. 21, 2012, now abandoned.

(30) Foreign Application Priority Data

Dec. 29, 2011 (EP) .................................... 11196121

(51) Int. Cl.
*A61K 31/18* (2006.01)
*A61K 31/00* (2006.01)
*A61K 31/05* (2006.01)
*A61K 31/132* (2006.01)
*A61K 31/196* (2006.01)
*A61K 31/198* (2006.01)
*A61K 31/352* (2006.01)
*A61K 31/365* (2006.01)
*A61K 31/473* (2006.01)
*A61K 31/565* (2006.01)
*A61K 31/4453* (2006.01)
*A61K 31/566* (2006.01)
*A61K 31/4402* (2006.01)
*A61K 45/06* (2006.01)
*G01N 33/68* (2006.01)
*A61K 31/64* (2006.01)
*C12Q 1/6881* (2018.01)

(52) U.S. Cl.
CPC .............. *A61K 31/18* (2013.01); *A61K 31/00* (2013.01); *A61K 31/05* (2013.01); *A61K 31/132* (2013.01); *A61K 31/196* (2013.01); *A61K 31/198* (2013.01); *A61K 31/352* (2013.01); *A61K 31/365* (2013.01); *A61K 31/4402* (2013.01); *A61K 31/4453* (2013.01); *A61K 31/473* (2013.01); *A61K 31/565* (2013.01); *A61K 31/566* (2013.01); *A61K 31/64* (2013.01); *A61K 45/06* (2013.01); *C12Q 1/6881* (2013.01); *G01N 33/6872* (2013.01); *C12Q 2600/136* (2013.01); *C12Q 2600/158* (2013.01); *G01N 2500/04* (2013.01)

(58) Field of Classification Search
CPC .. A61K 31/18; A61K 31/132; A61K 31/4453; A61K 31/566; A61K 31/365; A61K 31/473; A61K 31/4402; A61K 45/06; A61K 31/198; A61K 31/00; A61K 31/565; A61K 31/196; A61K 31/352; A61K 31/64; A61K 31/05
USPC ........................................................ 514/593
See application file for complete search history.

(56) References Cited

U.S. PATENT DOCUMENTS

| 6,187,756 | B1 | 2/2001 | Lee et al. |
| 8,236,847 | B2 | 8/2012 | Gougoutas et al. |
| 2008/0248099 | A1 | 10/2008 | Ishii |
| 2009/0137680 | A1* | 5/2009 | Simard ................ A61K 31/365 514/592 |

FOREIGN PATENT DOCUMENTS

ES 1782815 * 5/2005

OTHER PUBLICATIONS

Rasmussen et al. in Brain, 130, 2816-2829 (2007) (Year: 2007).*
Luzi et al. (1997) "Glibenclamide: An Old Drug with a Novel Mechanism of Action?", Acta Diabetol, 34:239-244.
Virgili, N. et al., "Oral adminislralion of the KATP channel opener diazoxide ameliorates disease progression in a murine model of multiple sclerosis", J. Neuroinflammation, 8:149 (2011).
Calabresi Peter A. (Apr. 23, 2002) "Considerations in the Treatment of Relapsing-Remitting Multiple Sclerosis", Neurology, 58(8 Suppl 4):S10-S22.
Goldberg et al. (Sep. 2009) "Comparing the Cost-Effectiveness of Disease-Modifying Drugs for the First-Line Treatment of Relapsing-Remitting Multiple Sclerosis", Journal of Managed Care Pharmacy, 15(7):543-555.

(Continued)

*Primary Examiner* — Yevgeny Valenrod
(74) *Attorney, Agent, or Firm* — Cozen O'Connor

(57) ABSTRACT

The invention relates to a compound which is effective in inhibiting the function of the TRPM4 ion channel and the use of such compound in treating or preventing a neurodegenerative disease, such as Multiple Sclerosis, Parkinson's disease, Alzheimer's disease, or amyotrophic lateral sclerosis, in a subject. The invention also provides a pharmaceutical composition comprising a TRPM4 inhibitory compound. The invention further relates to in vitro methods for identifying pharmaceutically active compounds that are useful for treating or preventing a neurodegenerative disease.

6 Claims, 7 Drawing Sheets
Specification includes a Sequence Listing.

(56) References Cited

OTHER PUBLICATIONS

Grand et al. (Apr. 1, 2008) "9-phenanthrol Inhibits Human TRPM4 but Not TRPM5 Cationic Channels", British Journal of Pharmacology, 153(8): 1697-1705.
Kagal et al. (Jan.-Mar. 2017) "Effect of Dipeptidyl Peptidase 4 Inhibitors on Acute And Subacute Models of Inflammation in Male Wistar Rats: An Experimental Study", International Journal of Applied and Basic Medical Research, 7(1):26-31.
Kim et al. (Aug. 2006) "Microglia, Major Player in the Brain Inflammation: Their Roles in The Pathogenesis of Parkinson's Disease", Experimental and Molecular Medicine, 38(4):333-347.

* cited by examiner

SEQUENCE LISTING

<160> NUMBER OF SEQ ID NOS: 3

<210> SEQ ID NO 1
<211> LENGTH: 1214
<212> TYPE: PRT
<213> ORGANISM: Homo sapiens

<400> SEQUENCE: 1

```
Met Val Val Pro Glu Lys Glu Gln Ser Trp Ile Pro Lys Ile Phe Lys
1               5                   10                  15

Lys Lys Thr Cys Thr Thr Phe Ile Val Asp Ser Thr Asp Pro Gly Gly
            20                  25                  30

Thr Leu Cys Gln Cys Gly Arg Pro Arg Thr Ala His Pro Ala Val Ala
        35                  40                  45

Met Glu Asp Ala Phe Gly Ala Ala Val Val Thr Val Trp Asp Ser Asp
    50                  55                  60

Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Gly Ser Gly Gly Pro
```

-continued

```
            115                 120                 125
Val Leu Gln Thr Trp Leu Gln Asp Leu Leu Arg Arg Gly Leu Val Arg
130                 135                 140
Ala Ala Gln Ser Thr Gly Ala Trp Ile Val Thr Gly Gly Leu His Thr
145                 150                 155                 160
Gly Ile Gly Arg His Val Gly Val Ala Val Arg Asp His Gln Met Ala
                165                 170                 175
Ser Thr Gly Gly Thr Lys Val Val Ala Met Gly Val Ala Pro Trp Gly
                180                 185                 190
Val Val Arg Asn Arg Asp Thr Leu Ile Asn Pro Lys Gly Ser Phe Pro
                195                 200                 205
Ala Arg Tyr Arg Trp Arg Gly Asp Pro Glu Asp Gly Val Gln Phe Pro
                210                 215                 220
Leu Asp Tyr Asn Tyr Ser Ala Phe Phe Leu Val Asp Asp Gly Thr His
225                 230                 235                 240
Gly Cys Leu Gly Gly Glu Asn Arg Phe Arg Leu Arg Leu Glu Ser Tyr
                245                 250                 255
Ile Ser Gln Gln Lys Thr Gly Val Gly Gly Thr Gly Ile Asp Ile Pro
                260                 265                 270
Val Leu Leu Leu Leu Ile Asp Gly Asp Glu Lys Met Leu Thr Arg Ile
                275                 280                 285
Glu Asn Ala Thr Gln Ala Gln Leu Pro Cys Leu Leu Val Ala Gly Ser
                290                 295                 300
Gly Gly Ala Ala Asp Cys Leu Ala Glu Thr Leu Glu Asp Thr Leu Ala
305                 310                 315                 320
Pro Gly Ser Gly Gly Ala Arg Gln Gly Glu Ala Arg Asp Arg Ile Arg
                325                 330                 335
Arg Phe Phe Pro Lys Gly Asp Leu Glu Val Leu Gln Ala Gln Val Glu
                340                 345                 350
Arg Ile Met Thr Arg Lys Glu Leu Leu Thr Val Tyr Ser Ser Glu Asp
                355                 360                 365
Gly Ser Glu Glu Phe Glu Thr Ile Val Leu Lys Ala Leu Val Lys Ala
                370                 375                 380
Cys Gly Ser Ser Glu Ala Ser Ala Tyr Leu Asp Glu Leu Arg Leu Ala
385                 390                 395                 400
Val Ala Trp Asn Arg Val Asp Ile Ala Gln Ser Glu Leu Phe Arg Gly
                405                 410                 415
Asp Ile Gln Trp Arg Ser Phe His Leu Glu Ala Ser Leu Met Asp Ala
                420                 425                 430
Leu Leu Asn Asp Arg Pro Glu Phe Val Arg Leu Leu Ile Ser His Gly
                435                 440                 445
Leu Ser Leu Gly His Phe Leu Thr Pro Met Arg Leu Ala Gln Leu Tyr
                450                 455                 460
Ser Ala Ala Pro Ser Asn Ser Leu Ile Arg Asn Leu Leu Asp Gln Ala
465                 470                 475                 480
Ser His Ser Ala Gly Thr Lys Ala Pro Ala Leu Lys Gly Gly Ala Ala
                485                 490                 495
Glu Leu Arg Pro Pro Asp Val Gly His Val Leu Arg Met Leu Leu Gly
                500                 505                 510
Lys Met Cys Ala Pro Arg Tyr Pro Ser Gly Gly Ala Trp Asp Pro His
                515                 520                 525
Pro Gly Gln Gly Phe Gly Glu Ser Met Tyr Leu Leu Ser Asp Lys Ala
                530                 535                 540
```

```
Thr Ser Pro Leu Ser Leu Asp Ala Gly Leu Gly Gln Ala Pro Trp Ser
545                 550                 555                 560

Asp Leu Leu Leu Trp Ala Leu Leu Leu Asn Arg Ala Gln Met Ala Met
                565                 570                 575

Tyr Phe Trp Glu Met Gly Ser Asn Ala Val Ser Ser Ala Leu Gly Ala
            580                 585                 590

Cys Leu Leu Arg Val Met Ala Arg Leu Glu Pro Asp Ala Glu Glu
            595                 600                 605

Ala Ala Arg Arg Lys Asp Leu Ala Phe Lys Phe Glu Gly Met Gly Val
610                 615                 620

Asp Leu Phe Gly Glu Cys Tyr Arg Ser Ser Glu Val Arg Ala Ala Arg
625                 630                 635                 640

Leu Leu Leu Arg Arg Cys Pro Leu Trp Gly Asp Ala Thr Cys Leu Gln
                645                 650                 655

Leu Ala Met Gln Ala Asp Ala Arg Ala Phe Phe Ala Gln Asp Gly Val
            660                 665                 670

Gln Ser Leu Leu Thr Gln Lys Trp Trp Gly Asp Met Ala Ser Thr Thr
            675                 680                 685

Pro Ile Trp Ala Leu Val Leu Ala Phe Cys Pro Pro Leu Ile Tyr
690                 695                 700

Thr Arg Leu Ile Thr Phe Arg Lys Ser Glu Glu Pro Thr Arg Glu
705                 710                 715                 720

Glu Leu Glu Phe Asp Met Asp Ser Val Ile Asn Gly Glu Gly Pro Val
                725                 730                 735

Gly Thr Ala Asp Pro Ala Glu Lys Thr Pro Leu Gly Val Pro Arg Gln
            740                 745                 750

Ser Gly Arg Pro Gly Cys Cys Gly Gly Arg Cys Gly Gly Arg Arg Cys
            755                 760                 765

Leu Arg Arg Trp Phe His Phe Trp Gly Ala Pro Val Thr Ile Phe Met
    770                 775                 780

Gly Asn Val Val Ser Tyr Leu Leu Phe Leu Leu Leu Phe Ser Arg Val
785                 790                 795                 800

Leu Leu Val Asp Phe Gln Pro Ala Pro Pro Gly Ser Leu Glu Leu Leu
                805                 810                 815

Leu Tyr Phe Trp Ala Phe Thr Leu Leu Cys Glu Glu Leu Arg Gln Gly
            820                 825                 830

Leu Ser Gly Gly Gly Gly Ser Leu Ala Ser Gly Gly Pro Gly Pro Gly
            835                 840                 845

His Ala Ser Leu Ser Gln Arg Leu Arg Leu Tyr Leu Ala Asp Ser Trp
            850                 855                 860

Asn Gln Cys Asp Leu Val Ala Leu Thr Cys Phe Leu Leu Gly Val Gly
865                 870                 875                 880

Cys Arg Leu Thr Pro Gly Leu Tyr His Leu Gly Arg Thr Val Leu Cys
            885                 890                 895

Ile Asp Phe Met Val Phe Thr Val Arg Leu Leu His Ile Phe Thr Val
            900                 905                 910

Asn Lys Gln Leu Gly Pro Lys Ile Val Ile Val Ser Lys Met Met Lys
            915                 920                 925

Asp Val Phe Phe Phe Leu Phe Phe Leu Gly Val Trp Leu Val Ala Tyr
    930                 935                 940

Gly Val Ala Thr Glu Gly Leu Leu Arg Pro Arg Asp Ser Asp Phe Pro
945                 950                 955                 960
```

-continued

Ser Ile Leu Arg Arg Val Phe Tyr Arg Pro Tyr Leu Gln Ile Phe Gly
            965                 970                 975

Gln Ile Pro Gln Glu Asp Met Asp Val Ala Leu Met Glu His Ser Asn
        980                 985                 990

Cys Ser Ser Glu Pro Gly Phe Trp Ala His Pro Pro Gly Ala Gln Ala
        995                 1000                1005

Gly Thr Cys Val Ser Gln Tyr Ala Asn Trp Leu Val Val Leu Leu
        1010                1015                1020

Leu Val Ile Phe Leu Leu Val Ala Asn Ile Leu Leu Val Asn Leu
        1025                1030                1035

Leu Ile Ala Met Phe Ser Tyr Thr Phe Gly Lys Val Gln Gly Asn
        1040                1045                1050

Ser Asp Leu Tyr Trp Lys Ala Gln Arg Tyr Arg Leu Ile Arg Glu
        1055                1060                1065

Phe His Ser Arg Pro Ala Leu Ala Pro Pro Phe Ile Val Ile Ser
        1070                1075                1080

His Leu Arg Leu Leu Arg Gln Leu Cys Arg Arg Pro Arg Ser
        1085                1090                1095

Pro Gln Pro Ser Ser Pro Ala Leu Glu His Phe Arg Val Tyr Leu
        1100                1105                1110

Ser Lys Glu Ala Glu Arg Lys Leu Leu Thr Trp Glu Ser Val His
        1115                1120                1125

Lys Glu Asn Phe Leu Leu Ala Arg Ala Arg Asp Lys Arg Glu Ser
        1130                1135                1140

Asp Ser Glu Arg Leu Lys Arg Thr Ser Gln Lys Val Asp Leu Ala
        1145                1150                1155

Leu Lys Gln Leu Gly His Ile Arg Glu Tyr Glu Gln Arg Leu Lys
        1160                1165                1170

Val Leu Glu Arg Glu Val Gln Gln Cys Ser Arg Val Leu Gly Trp
        1175                1180                1185

Val Ala Glu Ala Leu Ser Arg Ser Ala Leu Leu Pro Pro Gly Gly
        1190                1195                1200

Pro Pro Pro Pro Asp Leu Pro Gly Ser Lys Asp
        1205                1210

<210> SEQ ID NO 2
<211> LENGTH: 1069
<212> TYPE: PRT
<213> ORGANISM: Homo sapiens

<400> SEQUENCE: 2

Met Val Val Pro Glu Lys Glu Gln Ser Trp Ile Pro Lys Ile Phe Lys
1               5                   10                  15

Lys Lys Thr Cys Thr Thr Phe Ile Val Asp Ser Thr Asp Pro Gly Gly
                20                  25                  30

Thr Leu Cys Gln Cys Gly Arg Pro Arg Thr Ala His Pro Ala Val Ala
            35                  40                  45

Met Glu Asp Ala Phe Gly Ala Ala Val Val Thr Val Trp Asp Ser Asp
        50                  55                  60

Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Gly Ser Gly Gly Pro
115                 120                 125

Val Leu Gln Thr Trp Leu Gln Asp Leu Leu Arg Arg Gly Leu Val Arg
130                 135                 140

Ala Ala Gln Ser Thr Gly Ala Trp Ile Val Thr Gly Gly Leu His Thr
145                 150                 155                 160

Gly Ile Gly Arg His Val Gly Val Ala Val Arg Asp His Gln Met Ala
                165                 170                 175

Ser Thr Gly Gly Thr Lys Val Val Ala Met Gly Val Ala Pro Trp Gly
                180                 185                 190

Val Val Arg Asn Arg Asp Thr Leu Ile Asn Pro Lys Gly Ser Phe Pro
                195                 200                 205

Ala Arg Tyr Arg Trp Arg Gly Asp Pro Glu Asp Gly Val Gln Phe Pro
210                 215                 220

Leu Asp Tyr Asn Tyr Ser Ala Phe Phe Leu Val Asp Asp Gly Thr His
225                 230                 235                 240

Gly Cys Leu Gly Gly Glu Asn Arg Phe Arg Leu Arg Leu Glu Ser Tyr
                245                 250                 255

Ile Ser Gln Gln Lys Thr Gly Val Gly Gly Thr Gly Ile Asp Ile Pro
                260                 265                 270

Val Leu Leu Leu Leu Ile Asp Gly Asp Glu Lys Met Leu Thr Arg Ile
                275                 280                 285

Glu Asn Ala Thr Gln Ala Gln Leu Pro Cys Leu Leu Val Ala Gly Ser
290                 295                 300

Gly Gly Ala Ala Asp Cys Leu Ala Glu Thr Leu Glu Asp Thr Leu Ala
305                 310                 315                 320

Pro Gly Ser Gly Gly Ala Arg Gln Gly Glu Ala Arg Asp Arg Ile Arg
                325                 330                 335

Arg Phe Phe Pro Lys Gly Asp Leu Glu Val Leu Gln Ala Gln Val Glu
                340                 345                 350

Arg Ile Met Thr Arg Lys Glu Leu Leu Thr Val Tyr Ser Ser Glu Asp
                355                 360                 365

Gly Ser Glu Glu Phe Glu Thr Ile Val Leu Lys Ala Leu Val Lys Ala
370                 375                 380

Cys Gly Ser Ser Glu Ala Ser Ala Tyr Leu Asp Glu Leu Arg Leu Ala
385                 390                 395                 400

Val Ala Trp Asn Arg Val Asp Ile Ala Gln Ser Glu Leu Phe Arg Gly
                405                 410                 415

Asp Ile Gln Trp Arg Ser Phe His Leu Glu Ala Ser Leu Met Asp Ala
                420                 425                 430

Leu Leu Asn Asp Arg Pro Glu Phe Val Arg Leu Leu Ile Ser His Gly
                435                 440                 445

Leu Ser Leu Gly His Phe Leu Thr Pro Met Arg Leu Ala Gln Leu Tyr
450                 455                 460

Ser Ala Ala Pro Ser Asn Ser Leu Ile Arg Asn Leu Leu Asp Gln Ala
465                 470                 475                 480

Ser His Ser Ala Gly Thr Lys Ala Pro Ala Leu Lys Gly Gly Ala Ala
                485                 490                 495

Glu Leu Arg Pro Pro Asp Val Gly His Val Leu Arg Met Leu Leu Gly
                500                 505                 510

Lys Met Cys Ala Pro Arg Tyr Pro Ser Gly Gly Ala Trp Asp Pro His
                515                 520                 525

```
Pro Gly Gln Gly Phe Gly Glu Ser Met Tyr Leu Leu Ser Asp Lys Ala
        530             535                 540
Thr Ser Pro Leu Ser Leu Asp Ala Gly Leu Gly Gln Ala Pro Trp Ser
545             550                 555                 560
Asp Leu Leu Leu Trp Ala Leu Leu Leu Asn Arg Ala Gln Met Ala Met
                565                 570                 575
Tyr Phe Trp Glu Met Gly Ser Asn Ala Val Ser Ser Ala Leu Gly Ala
            580                 585                 590
Cys Leu Leu Leu Arg Val Met Ala Arg Leu Glu Pro Asp Ala Glu Glu
                595                 600                 605
Ala Ala Arg Arg Lys Asp Leu Ala Phe Lys Phe Glu Gly Met Gly Val
    610                 615                 620
Asp Leu Phe Gly Glu Cys Tyr Arg Ser Ser Glu Val Arg Ala Ala Arg
625                 630                 635                 640
Leu Leu Leu Arg Arg Cys Pro Leu Trp Gly Asp Ala Thr Cys Leu Gln
                645                 650                 655
Leu Ala Met Gln Ala Asp Ala Arg Ala Phe Phe Ala Gln Asp Gly Val
                660                 665                 670
Gln Ser Leu Leu Thr Gln Lys Trp Trp Gly Asp Met Ala Ser Thr Thr
            675                 680                 685
Pro Ile Trp Ala Leu Val Leu Ala Phe Phe Cys Pro Pro Leu Ile Tyr
        690                 695                 700
Thr Arg Leu Ile Thr Phe Arg Lys Ser Glu Glu Pro Thr Arg Glu
705                 710                 715                 720
Glu Leu Glu Phe Asp Met Asp Ser Val Ile Asn Gly Glu Gly Pro Val
                725                 730                 735
Gly Leu Thr Pro Gly Leu Tyr His Leu Gly Arg Thr Val Leu Cys Ile
            740                 745                 750
Asp Phe Met Val Phe Thr Val Arg Leu Leu His Ile Phe Thr Val Asn
                755                 760                 765
Lys Gln Leu Gly Pro Lys Ile Val Ile Val Ser Lys Met Met Lys Asp
    770                 775                 780
Val Phe Phe Phe Leu Phe Phe Leu Gly Val Trp Leu Val Ala Tyr Gly
785                 790                 795                 800
Val Ala Thr Glu Gly Leu Leu Arg Pro Arg Asp Ser Asp Phe Pro Ser
            805                 810                 815
Ile Leu Arg Arg Val Phe Tyr Arg Pro Tyr Leu Gln Ile Phe Gly Gln
                820                 825                 830
Ile Pro Gln Glu Asp Met Asp Val Ala Leu Met Glu His Ser Asn Cys
            835                 840                 845
Ser Ser Glu Pro Gly Phe Trp Ala His Pro Pro Gly Ala Gln Ala Gly
    850                 855                 860
Thr Cys Val Ser Gln Tyr Ala Asn Trp Leu Val Val Leu Leu Leu Val
865                 870                 875                 880
Ile Phe Leu Leu Val Ala Asn Ile Leu Leu Val Asn Leu Leu Ile Ala
                885                 890                 895
Met Phe Ser Tyr Thr Phe Gly Lys Val Gln Gly Asn Ser Asp Leu Tyr
            900                 905                 910
Trp Lys Ala Gln Arg Tyr Arg Leu Ile Arg Glu Phe His Ser Arg Pro
    915                 920                 925
Ala Leu Ala Pro Pro Phe Ile Val Ile Ser His Leu Arg Leu Leu Leu
    930                 935                 940
Arg Gln Leu Cys Arg Arg Pro Arg Ser Pro Gln Pro Ser Ser Pro Ala
```

-continued

```
            945                 950                 955                 960
Leu Glu His Phe Arg Val Tyr Leu Ser Lys Glu Ala Glu Arg Lys Leu
                    965                 970                 975

Leu Thr Trp Glu Ser Val His Lys Glu Asn Phe Leu Leu Ala Arg Ala
                980                 985                 990

Arg Asp Lys Arg Glu Ser Asp Ser Glu Arg Leu Lys Arg Thr Ser Gln
            995                 1000                1005

Lys Val Asp Leu Ala Leu Lys Gln Leu Gly His Ile Arg Glu Tyr
    1010                1015                1020

Glu Gln Arg Leu Lys Val Leu Glu Arg Glu Val Gln Gln Cys Ser
        1025                1030                1035

Arg Val Leu Gly Trp Val Ala Glu Ala Leu Ser Arg Ser Ala Leu
        1040                1045                1050

Leu Pro Pro Gly Gly Pro Pro Pro Asp Leu Pro Gly Ser Lys
        1055                1060                1065

Asp

<210> SEQ ID NO 3
<211> LENGTH: 21
<212> TYPE: PRT
<213> ORGANISM: artificial
<220> FEATURE:
<223> OTHER INFORMATION: myelin oligodendrocyte glycoprotein peptide
      35-55 (MOG35-55)

<400> SEQUENCE: 3

Met Glu Val Gly Trp Tyr Arg Ser Pro Phe Ser Arg Val Val His Leu
1               5                   10                  15

Tyr Arg Asn Gly Lys
            20
```

METHOD OF TREATING OR PREVENTING NEURODEGENERATION

INCORPORATION BY REFERENCE OF SEQUENCE LISTING

The instant application contains a Sequence Listing file entitled 058223-502C02US_SL.txt, with a file size of about 20,391 bytes in size and created on our about Dec. 1, 2020, has been submitted electronically in ASCII format and is hereby incorporated by reference in its entirety.

BACKGROUND OF THE INVENTION

Neurodegenerative diseases of the central nervous system (CNS) which cause progressive loss of neuronal structure and function are particularly devastating diseases for the affected patients and their families. Among these neurodegenerative diseases are, for example, Multiple Sclerosis (MS), Parkinson's disease, Alzheimer's disease, amyotrophic lateral sclerosis (ALS) and stroke. Due to the complexity of the CNS many of these diseases are only poorly understood to date.

One of the most common progressive neurodegenerative diseases is Multiple Sclerosis (MS). MS is a chronic inflammatory, demyelinating disease of the CNS and the leading cause of neurological disability in young adults. It affects approximately 2.5 million individuals worldwide and currently no curative treatment is available. The pathogenesis of MS has been attributed to a breakdown of T lymphocyte tolerance to CNS self-antigens resulting in chronic inflammation with subsequent demyelination and neuro-axonal degeneration (Compston, A. and Coles A. (2008) *Lancet.* 372:1502-1517). Axonal damage arises already early in the disease, also independent of demyelination and correlates best with clinical disability during the progressive course of MS (Kornek et al. (2000), *Am J Pathol.* 157:267-276). Similarly, neuronal damage and atrophy of the gray matter, with a predilection for the cingulate gyrus, the fronto-temporal cortices and the hippocampus, have also been shown to occur from the earliest stages and are likely to play an important role in clinical progression (Fisher et al. (2008), *Ann Neurol.* 64:255-265).

While the pathophysiological mechanisms leading to neuro-axonal injury during chronic inflammation of the CNS are still ill defined, it has been suggested that chronic CNS inflammation is associated with an increased oxidative stress and release of glutamate, which results in axonal and neuronal injury by inducing mitochondrial dysfunction and increased metabolic demand. This creates a chronic state of virtual hypoxia with ensuing changes in ion homeostasis (Frischer et al. (2009) *Brain.* 132:1175-1189). Indeed, damaged and respiratory-deficient mitochondria as well as reduced ATP production can be detected in neuronal cells in MS lesions (Campbell et al. (2011), *Ann Neurol.* 69:481-492; Dutta et al. (2006), *Ann Neurol.* 59:478-489; Mahad et al. (2009), *Brain.* 132:1161-1174). In addition, glutamate receptor activation by release of glutamate in MS lesions and experimental autoimmune encephalomyelitis (EAE) inflammatory infiltrates with subsequent $Ca^{2+}$ overload have been shown to occur in axons and neurons under inflammation-induced hypoxic conditions (Pitt et al. (2000), *Nat Med.* 6:67-70). However, the downstream mechanisms, which are initiated by ATP shortage and $Ca^{2+}$ overload culminating in a sustained influx of cations and eventually leading to neuro-axonal degeneration, remain elusive (Stirling et al. (2010), *Trends Mol Med.* 16:160-170).

A major factor by which neurodegeneration in MS occurs is due to an imbalanced glutamate metabolism with an increased extracellular glutamate concentration. Glutamate is released by activated immune cells and damaged CNS cells; indeed, cerebrospinal fluid glutamate levels are increased in relapsing-remitting MS during relapse and during clinical progression in secondary progressive MS (Stover et al. (1997), *Eur J Clin Invest.* 27:1038-1043; Sarchielli et al. (2003), *Arch Neurol.* 60:1082-1088). An increase in extracellular glutamate levels causes excitotoxic neurodegeneration through ionotropic glutamate receptors such as NMDA- and AMPA-receptors by eliciting $Ca^{2+}$ and $Na^+$ influx. Accordingly, glutamate receptor antagonists were somewhat efficient in reducing neuro-axonal damage in EAE (Basso et al. (2008), *J Clin Invest.* 118:1532-1543).

The transient receptor potential channel of the melastatin subfamily TRPM4 provides a persistent cation influx combined with gating properties, which are associated with alterations of energy metabolism and ion homeostasis (Guinamard et al. (2010), *Physiology (Bethesda).* 25:155-164). TRPM4 is a voltage-dependent $Ca^{22+}$-impermeable cation channel with a unitary conductance of 25 pS that is activated by a rise in intracellular calcium (Launay et al. (2002) *Cell.* 109:397-407), whereas intracellular ATP inhibits TRPM4 activity and regulates TRPM4 $Ca^{2+}$ sensitivity (Nilius et al. (2005), *J Biol Chem.* 280:6423-6433). Further, phosphatidylino-sitol-4,5-bisphosphate and hydrogen peroxide (Simon et al. (2011), *J Biol Chem.* 285:37150-37158) remove TRPM4 channel desensitization during $Ca^{2+}$ stimulation. Channel opening leads to the conduction of monovalent cations with $Na^+$ as the main charge carrier (Launay et al. (2002), *Cell.* 109:397-407). TRPM4 is expressed in different tissues including the heart, arteries, gastrointestinal tract and immune system. It controls T cell, dendritic cell and mast cell activation or migration through regulating membrane depolarization and $Ca^{2+}$ homeostasis. Pathologically, TRPM4 has been associated with hypertension, secondary hemorrhage after spinal cord injury, hyper-IgE syndrome and cardiac conduction dysfunction (Mathar et al. (2010), *J Clin Invest.* 120:3267-3279; Gerzanich et al. (2009), *Nat Med.* 15:185-191; Kruse et al. (2009), *J Clin Invest.* 119: 2737-2744). *Trpm4* mRNA was found to be present in brain tissue, and a suggestive TRPM4-mediated current was recorded in the brain stem (Mironov (2008), *J Physiol.* 586:2277-2291). Inhibition of TRPM4 has been suggested to prevent progressive hemorrhagic necrosis after spinal cord injury (US 2010/0092469 A1). Expression of the TRPM4 ion channel was up-regulated in capillary epithelial cells after spinal cord injury, leading to capillary leakiness and failure of capillary integrity. However, functional neuronal expression and a contribution of TRPM4 to neurodegeneration in diseases like MS have thus far not been shown or otherwise suggested.

The present inventors surprisingly found that TRPM4 is expressed in neuronal somata and axons in mice suffering from Experimental Autoimmune Encephylomyelitis (EAE) and in MS lesions of human patients. In addition, it could be demonstrated that TRPM4 is directly involved in mediating neuronal-axonal degeneration under neuroinflammatory conditions, such as in MS. Moreover, the present application provides evidence that inhibitors of the TRPM4 channel protein are capable of preventing neuro-axonal injury in the inflamed CNS without affecting the encephalitogenic immune response.

The present invention therefore provides a new and widely applicable therapeutic strategy for preventing neurodegeneration in a number of different diseases and conditions which are known to be associated with neurodegeneration, amongst others, Multiple Sclerosis.

BRIEF SUMMARY OF THE INVENTION

The invention relates to a compound which is effective in inhibiting the function of the TRPM4 ion channel and the use of such compound in treating or preventing a neurodegenerative disease, such as Multiple Sclerosis, Parkinson's disease, Alzheimer's disease, or amyotrophic lateral sclerosis, in a subject. The invention also provides a pharmaceutical composition comprising a TRPM4 inhibitory compound. The invention further relates to in vitro methods for identifying pharmaceutically active compounds that are useful for treating or preventing a neurodegenerative disease.

BRIEF DESCRIPTION OF THE DRAWINGS

In FIGS. 5a and b results are presented as mean values±s.e.m. of four independent experiments; statistical analyses were performed by two-way ANOVA with Bonferonni posthoc test; asterisks indicate statistical significance; *P<0.05, **P<0.01. Results in FIGS. 5d, c and e are shown as mean values±s.e.m. of two independent experiments each; asterisks indicate statistical significance of student's t-test; *P0.05, **P<0.01.

DETAILED DESCRIPTION OF THE INVENTION

Figure 1:
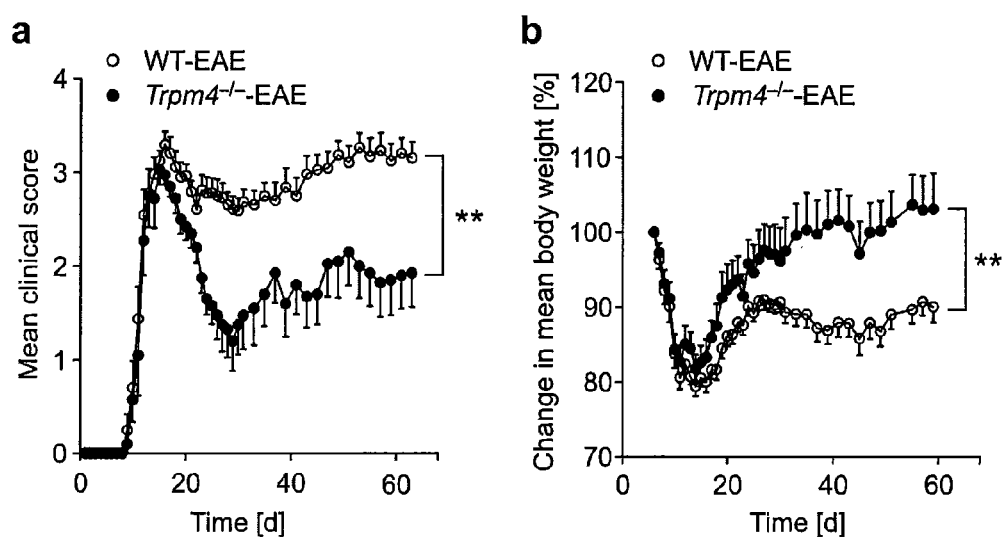
FIG. 1 shows that Trpm4 deletion ameliorates disease severity in EAE mice. Clinical scores (a) and body weight changes (b) for groups of WT EAE (n=15) and Trpm4$^{-/-}$ EAE (n=10) mice after immunization with MOG$_{35-55}$ are shown as mean values±s.e.m; asterisks indicate statistical significance; **P<0.01. Results from one representative experiment out of three are shown.

The present invention is amongst other things based on the insight that blocking the TRPM4 ion channel confers resistance of axons and neurons towards hostile challenges which results in neuro-axonal preservation and less clinical disability and neurodegeneration. Therefore, the present invention specifically contemplates to use antagonists and/or inhibitors of the TRPM4 ion channel for treating a neurodegenerative disease by preventing neuronal loss in a subject. Compounds that interfere with the function of the TRPM4 ion channel have been extensively described in the art. However, the use of such compounds for treating a neurodegenerative disease has not yet been suggested.

Thus, in a first aspect the invention relates to a compound which is effective in inhibiting the function of a TRPM4 ion channel for use in a method of treating or preventing a neurodegenerative disease in a subject. More specifically, the invention relates to such an inhibitory compound for use in a method of preventing neuronal damage and/or loss in a subject suffering from a neurodegenerative disease. As used herein, the "function of a TRPM4 ion channel" means the capability of the protein to regulate the influx of ions into the cell, in particular the influx of cations such as Na$^+$. Accordingly, a "functional" TRPM4 ion channel refers to a channel protein that effectively regulates the influx of ions, such as Nat, into the cell The present invention is hence useful for treating or ameliorating the effects of neurodegenerative diseases which are associated with TRPM4-mediated cytotoxicity.

The compounds of the present invention effectively prevent damage and/or loss of neurons in the nervous system (NS) of a subject, preferably in the central nervous system (CNS) of a subject. As used herein, the NS is to be understood as being composed of the CNS and the peripheral nervous system. Further, as used herein, the CNS is to be understood as containing the brain and the spinal cord. In a preferred embodiment, the compounds of the invention are administered for preventing damage and/or loss of neurons in the brain. In a further embodiment, progressive damage and/or loss of neurons may be halted by administration of the compounds of the invention. Halting the damage and/or the loss of neurons means that the pathological processes of the neurodegenerative disease which finally result in damage and/or loss of neurons are stopped or at least reduced.

The neurodegenerative disease to be treated or prevented according to the invention may be any known neurodegenerative disease, preferably one that is associated with inflammation. As used herein a neurodegenerative disease is a non-traumatic, disease which is associated with the progressive loss of functional neurons in the NS, preferably the CNS. The neurodegenerative disease to be treated according to the invention may be caused by a genetic predisposition. Conditions of the NS elicited traumatic events and/or physical shock, such as traumatic brain injury, cerebral ischemia, hypoxia and edema are not understood as neurodegenerative diseases in the sense of the present invention.

Further, it has been found that TRPM4 signaling contributes to glutamate excitotoxicity which has devastating effects in a large number of neurodegenerative diseases. Therefore, the compounds, methods and uses of the present invention will be particularly useful in the treatment of neurodegenerative diseases which have been associated with glutamate excitotoxicity.

Thus, according to a preferred embodiment, the neurodegenerative disease to be treated or prevented according to the invention is known to be associated with glutamate excitotoxicity. As used herein, glutamate excitotoxicity refers to a process that results in damaging or killing neuronal and/or axonal cells by excessive stimulation of these cells by glutamate and other substances that are capable of activating the glutamate receptor. Thus, glutamate excitotoxicity occurs as a result from overactivation of glutamate receptors. For example, the neurodegenerative disease known to be associated with glutamate excitotoxicity may be selected from the group Multiple Sclerosis (MS), such as relapsing remitting MS or secondary progressive MS, Parkinson's disease, Alzheimer's disease, and amyotrophic lateral sclerosis. In a particularly preferred embodiment, the neurodegenerative disease is MS.

The compounds of the present invention are pharmaceutically active compounds which are effective in decreasing the expression and/or the activity of the TRPM4 ion channel protein. The compounds can include all different types of organic or inorganic molecules, including peptides, polypeptides, oligo- or polysaccharides, fatty acids, steroids, and the like. Typically, the compounds will be small molecules with a molecular weight of less than about 2,500 daltons, less than 2000 daltons, less than 1500 daltons, less than 1000 daltons, or less than 500 daltons. In a particularly preferred embodiment of the invention the compounds which inhibit the function of TRPM4 ion channel have a molecular weight of less than about 500 daltons.

Preferably, the compounds of the present invention are able to cross the blood-brain barrier, i.e. they are blood-brain barrier-permeable. This means that the compounds are able to reach a site in the brain which is affected by neuronal injury and/or loss. Inhibitory compounds with a molecular weight of below 500 daltons are particularly suitable, since they are often able to cross the blood-brain barrier, or their transport across the blood-brain barrier is achieved by other means, such as by transporters or by hydrophobic stretches in the compound which allow diffusion across the blood-brain barrier.

The compounds contemplated by the invention affect the function of a TRPM4 ion channel protein. In a preferred embodiment, the inhibitory compounds interfere with the human TRPM4 ion channel protein. In the context of the present invention, the terms "TRPM4 ion channel" or "TRPM4" refer to the calcium-activated transient receptor potential melastatin 4 cation channel. TRPM4 belongs to the family of transient receptor potential cation channels, and more specifically to the subfamily M of this family of cation channels. The human TRPM4 protein occurs in two different isoforms that are depicted in SEQ ID NO:1 (NP_060106) and SEQ ID NO:2 (NP_001182156).

Preferably, the compounds contemplated by the invention inhibit the function of an TRPM4 ion channel having an amino acid sequence as depicted in SEQ ID NO:1 (NP_060106) or an amino acid sequence having at least 90% sequence identity to the sequence of SEQ ID NO:1 (NP_060106). In a further preferred embodiment, the compounds contemplated by the invention inhibit the function of an TRPM4 ion channel having an amino acid sequence as depicted in SEQ ID NO:2 (NP_060106) or an amino acid sequence having at least 90% sequence identity to the sequence of SEQ ID NO:2 (NP_001182156). Further isoforms of the human TRPM4 protein which retain the ion channel activity may also be inhibited by the compounds of the present invention.

The compounds which are contemplated herein for treating and/or preventing a neurodegenerative disease are effective in inhibiting the function of the TRPM4 ion channel. This means that the compounds effectively reduce the extent of membrane current that occurs due to the influx of cations upon opening of the channel. In a preferred embodiment, the compound decreases the TRPM4 ion channel activity by at least 10%, 20%, 30%, 40%, 50%, 60%, 70%, 80%, 90%, or 95% compared to the activity in the absence of the compound. In a particularly preferred embodiment, the inhibitory compound blocks the TRPM4 ion channel, i.e. the channel is completely deactivated so that there is no detectable influx of cations, such as Na$^+$. The compounds preferably act by interacting with or binding to the TRPM4 protein, thereby preventing the sterical changes in the channel protein that occur upon opening of the channel, e.g. in response to an increase in the intracellular Ca$^{2+}$ concentration. Compounds that actively bind to TRPM4 may bind to the extracellular, the intracellular or the transmembrane part of the TRPM4 ion channel protein.

Preferably, the inhibitory compound is specific for the TRPM4 ion channel, i.e. the compound inhibits the expression and/or activity of the TRPM4 ion channel, while it does essentially not inhibit the expression and/or activity of other proteins or enzymes, e.g. other ion channels. As a result of the TRMP4 specificity, the compounds according to the invention elicit no or only tolerable side effects when administered to a subject.

The subject to be treated with the inhibitory compound will normally be a mammal, and preferably is a human. Generally, the subject can be of any age. The subject preferably suffers from a neurodegenerative disease, more preferably from a progressive neurodegenerative disease. The subject may be in any stage of the disease, i.e. the disease may be in an early stage wherein the subject shows only the first pathological signs that are normally associated with said disease, or the subject may be in a late stage of the disease. The subject to be treated may have a genetic or other predisposition for developing a neurodegenerative disease in the future.

The TRPM4-inhibitory compound of the invention can be derived from different groups of molecules. For example, TRPM4-inhibitory compounds can include antisense polynucleotides which bind to the gene encoding the TRPM4 ion channel and block transcription, RNA processing and/or translation of said gene. The antisense molecules can be RNA or DNA molecules. Also, the TRPM4-inhibitory compound of the invention can be a RNA molecule which exerts its effect by RNA interference. Examples for such compounds are RNAi molecules and siRNA molecules that are capable of blocking translation of the TRPM4-encoding mRNA. Alternatively, the TRPM4-inhibitory compound of the invention can be a ribozyme that cleaves the TRPM4-encoding mRNA. Other classes of molecules which may give rise to suitable TRPM4-inhibitory compounds include peptides, antibodies and antibody fragments. Peptides that bind and interfere with the TRPM4 channel protein may be conveniently screened in random peptide libraries.

A number of inhibitors of TRPM4 have been described in the art. For example, nucleotides such as ATP, ADP, AMP, AMP-PNP, and adenosine have been described to inhibit the TRPM4 ion channel quickly and reversibly. Similarly, polyamines like spermine have also been found to block TRPM4 currents (Nilius et al. (2004), Eur J Physiol. 448: 70-75).

Other compounds that have been described to inhibit the TRPM4 ion channel are those referred to in WO 2006/034048 and WO 03/079987. These compounds include antagonists to sulfonylurea receptor-1 (SUR1), such as 9-phenanthrol, glibenclamide, tolbutamide, repaglinide, nateglinide, meglitinide, midaglizole, LY397364, LY389382, glyclazide, glimepiride, estrogen, and estrogen-related compounds (such as estradiol, estrone, estriol, genistein, nonsteroidal estrogen, phytoestrogen, zearalenone, and the like). The above compounds can be substituted or otherwise modified at one or more sites, as long as these modifications do not substantially impair the TRPM4-inhibitory effect of the compounds and do not result in any undesired toxic side effects.

In a preferred embodiment of the invention, the TRPM4-inhibitory compound for use in treating or preventing a neurodegenerative disease is 9-phenanthrol or a pharmaceutically acceptable salt, solvate, tautomer or ester thereof. Examples of pharmaceutically acceptable salts of 9-phenanthrol include hydrochlorides and sulphates. 9-phenanthrol is a metabolite of phenanthrene, and the IUPAC name is phenanthren-9-ol. The structure of 9-phenanthrol is as follows:

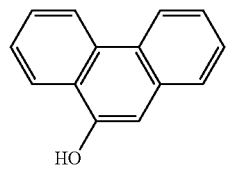

The above structure can be substituted or otherwise modified at one or more sites, as long as these modifications do not substantially impair the TRPM4-inhibitory effect of 9-phenanthrol and do not result in any undesired toxic side effects. For example, one or more hydrogen atoms of the C—H bonds of the heterocyclic ring system can be substituted with halogen atoms, such as chlorine, bromine or iodine atoms. Further, the hydrogen of the C—H bonds can also be replaced by an alkyl group, such as methyl, ethyl or propyl.

In another particularly preferred embodiment of the invention, the TRPM4-inhibitory compound for use in treating or preventing a neurodegenerative disease is glibenclamide or a pharmaceutically acceptable salt, solvate, tautomer or ester thereof. Examples of pharmaceutically acceptable salts of glibenclamide include in particular hydrochlorides and sulphates. Glibenclamide has been described as a modulator of ATP binding cassette proteins (ABC transporters). The IUPAC name for glibenclamide is N-(44N-(cyclohexylcarbamoyl)sulfamoyllphenethyl)-2-methoxybenzamide. It has the following structure:

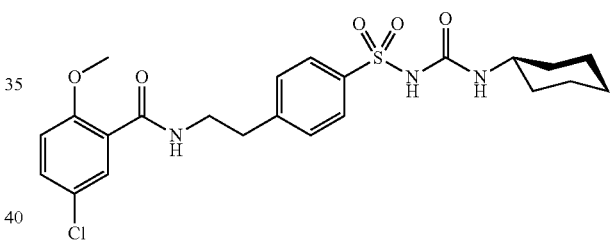

The person skilled in the art will understand that the structure described above can be substituted or otherwise modified at one or more sites, as long as these modifications do not substantially impair the TRPM4-inhibitory effect of glibenclamide and do not result in any undesired toxic side effects. For example, one or more hydrogen atoms of the C—H bonds of the heterocyclic ring system can be substituted with halogen atoms, such as chlorine, bromine or iodine atoms. Further, the hydrogen of the C—H bonds can also be replaced by an alkyl group, such as methyl, ethyl or propyl.

The TRPM4-inhibitory compound of the present invention as described above will normally be provided in the form of a pharmaceutical composition which also comprises one or more excipients, carriers and/or diluents which are suitable for the intended way of administration. Generally, the compound may be administered in any suitable form that does not interfere with its TRPM4-inhibitory activity. The preferred route of administration will depend inter alia on the location of the neurodegeneration to be treated. For example, the compound may be administered orally in the form of tablets, capsules, granule, powder, liquids, and the like. Alternatively, the TRPM4-inhibitory compound may be formulated for being administered parenterally, e.g. by intravenous injection or intravenous infusion. In a preferred aspect, the TRPM4-inhibitory compound is administered to the subject by intravenous infusion, more preferably by short-term infusion within less than 60 min, e.g. within 30 min, 20 min or 15 min.

Compositions suitable for injection and/or infusion include solutions or dispersions and powders for the extemporaneous preparation of such injectable solutions or dispersions. The composition for injection must be sterile and should be stable under the conditions of manufacturing and storage. Preferably, the compositions for injection and/or infusion also include a preservative, such as a chlorobutanol, phenol, ascorbic acid, thimerosal, and the like. For intravenous administration, suitable carriers may comprise physiological saline, bacteriostatic water, Cremophor EL™ (BASF) or phosphate-buffered saline (PBS). Sterile solutions for injection and/or infusion can be prepared by incorporating the TRPM4-inhibitory compound in the required amount in an appropriate solvent followed by filter sterilization.

The pharmaceutical compositions of the present invention will comprise an amount of the TRPM4-inhibitory compound that is effective to inhibit the TRPM4 ion channel, thereby reducing the extent of neurodegeneration by protecting the NS, preferably the CNS, from neuronal loss. The therapeutically effective amount of the TRPM4-inhibitory compound to be administered will depend on several parameters, such as the mode of administration, the particular neurodegenerative disease to be treated, the severity of the disease, the history of the disease, the age, height, weight, health, and physical condition of the individual to be treated, and the like. A therapeutically effective amount of the TRPM4-inhibitory compound can be determined by one of ordinary skill in the art without undue experimentation given the disclosure set forth herein.

The TRPM4-inhibitory compound will preferably be administered to a subject in an amount that ranges from 0.1 μg/kg body weight to 10,000 μg/kg body weight, e.g. from 0.5 μg/kg to 7,500 μg/kg body weight, from 1.0 μg/kg to 5,000 μg/kg body weight, from 5.0 μg/kg to 3,000 μg/kg body weight, from 7.5 μg/kg to 2,500 μg/kg body weight, from 10 μg/kg to 2,000 μg/kg body weight, from 25 μg/kg to 1,500 μg/kg body weight, from 50 μg/kg to 1,000 μg/kg body weight, from 100 μg/kg to 800 μg/kg body weight, from 300 μg/kg to 600 μg/kg body weight, and more preferably from 400 μg/kg to 500 μg/kg body weight.

Apart from the TRPM4-inhibitory compound, the pharmaceutical composition provided by the present invention may further comprise other anti-neurodegenerative or anti-inflammatory compounds which are commonly used in the treatment of neurodegenerative diseases, such as interferon beta-1a, interferon beta-1b, fampridine, fingolimod hydrochloride, natalizumab, glatiramer acetate, or mitoxantrone. Where the TRPM4-inhibitory compound is used in combination with another anti-neurodegenerative agent, the two active ingredients can be administered to the subject in the form of a single pharmaceutical composition comprising both agents and pharmaceutically acceptable excipients and carriers. Administration of such a pharmaceutical composition will automatically result in a simultaneous administration of both agents. Alternatively, the two therapeutic agents may also be administered separately from each other, i.e. in the form of two separate pharmaceutical compositions, one containing the TRPM4-inhibitory compound, and the other containing the additional anti-neurodegenerative or anti-inflammatory agent. The two separate compositions can be administered simultaneously, i.e. at the same time at two distinct sites of administration, or they may be administered sequentially (in either order) to the same site or to different sites of administration.

Preferably, both the composition comprising the TRPM4-inhibitory compound and the composition comprising the second anti-neurodegenerative or anti-inflammatory agent are administered according to a weekly dosing regimen, more preferably a regimen in which a single dose of the TRPM4-inhibitory compound and a single dose of the anti-neurodegenerative or anti-inflammatory agent is administered every week for a treatment period of 2 or more weeks, for example, 3, 4, 5, 6, 7, 8, 9, 10, 11, 12, 13, 14, 15, 16, 17, 18, 19, 20, or more weeks. Preferably, the treatment period comprises at least 12 weeks. It will also be possible to administer the overall weekly dose of the TRPM4-inhibitory compound and/or the anti-neurodegenerative or anti-inflammatory agent in more than one administration per week, e.g. in 2 or 3 administrations per week. In a preferred embodiment, the amount of the TRPM4-inhibitory compound to be administered weekly is delivered as a single intravenous infusion per week, and the amount of the anti-neurodegenerative or anti-inflammatory agent to be administered weekly is also given as a single intravenous infusion per week, either at the same day of administration of the TRPM4-inhibitory compound, e.g. within about 10 minutes to about 6 hours after administration of the TRPM4-inhibitory compound has been completed, more preferably within about 30, 60, 90, 120, 150, 180, 210 or 240 minutes, or at any of days 2, 3, 4, 5, 6 or 7 of the week.

For example, a combination therapy with the above-mentioned agents that is based on a weekly dosing regimen begins on day 1 of a treatment period, and a first therapeutically effective dose of the TRPM4-inhibitory compound is administered at that day. A first therapeutically effective dose of the additional anti-neurodegenerative or anti-inflammatory agent can be administered either on the same day, e.g. simultaneously or within about 30, 60, 90, 120, 150, 180, 210 or 240 minutes after administration of the TRPM4-inhibitory compound. Alternatively, the additional anti-neurodegenerative or anti-inflammatory agent can be administered at any of days 2, 3, 4, 5, 6 or 7 of the first week. At day 8, a second therapeutically effective dose of the TRPM4-inhibitory compound is administered accompanied or followed by the second administration of the additional anti-neurodegenerative or anti-inflammatory agent. The skilled person will readily be able to design other administration regimens which are suitable for the delivery of the combined active ingredients.

The insight that a decreased expression of the TRPM4 gene and/or a decreased activity of the TRPM4 cation channel prevents or halts neurodegenerative disease in the NS, preferably the CNS of a subject allows the design of screening assays which identify pharmaceutically active compounds which are effective in preventing or halting neurodegenerative disease in the NS, preferably the CNS, of a subject.

In a further aspect, the present invention therefore provides methods for identifying a pharmaceutically active compound that could be used for treating or preventing neurodegenerative diseases. The methods of the present invention can therefore be used for drug screening approaches that aim to identify new pharmaceutically active for treating diseases, such as Alzheimer's disease or MS.

Accordingly, the invention relates to an in vitro method for identifying a pharmaceutically active compound for treating or preventing an inflammatory, neurodegenerative disease in a subject, comprising (a) contacting a candidate compound with a functional TRPM4 ion channel;
(b) detecting whether said candidate compound interferes with the function of the TRPM4 ion channel;

wherein a compound which inhibits the function of the TRPM4 ion channel is suitable for treating or preventing said inflammatory, neurodegenerative disease. The neurodegenerative disease is preferably one that is associated with glutamate excitotoxicity. More preferably, it is selected from the group consisting of MS, Parkinson's disease, Alzheimer's disease, and amyotrophic lateral sclerosis, wherein MS is particularly preferred.

A decrease in the activity of the TRPM4 ion channel, i.e. in its capability of regulating cation influx, may be determined by any suitable assay. For example, a pharmaceutically active compound which inhibits the TRPM4 ion channel leads to a reduction in the inward current that can be measured in whole-cell patch-clamp recordings after the addition of glutamate. A method suitable for detecting whether a given candidate compound interferes with the function of the TRPM4 ion channel is disclosed in the below Example 7. A different method could employ the measurement of cation-sensitive fluorescent probes, which were previously loaded into the respective cells.

In an alternative approach, the screening can target compounds which interfere with TRPM4 transcription and/or translation. In these embodiments, an in vitro method is provided for identifying a pharmaceutically active compound for treating or preventing an inflammatory, neurodegenerative disease in a subject, comprising (a) contacting a candidate compound with a cell that expresses a functional TRPM4 ion channel;
(b) detecting whether said candidate compound decreases the transcription of the TRPM4 gene and/or the translation of the TRPM4 mRNA; wherein a compound which decreases the transcription of the TRPM4 gene and/or the translation of the TRPM4 mRNA is suitable for treating or preventing said inflammatory, neurodegenerative disease. Again, the neurodegenerative disease is preferably a disease that is associated with glutamate excitotoxicity. More preferably, it is selected from the group consisting of MS, Parkinson's disease, Alzheimer's disease, and amyotrophic lateral sclerosis, wherein MS is particularly preferred.

Screening methods which monitor the transcription of the TRPM4 gene and/or the translation of the TRPM4 mRNA are particularly useful, e.g. for identifying compounds which inhibit the TRPM4 ion channel by decreasing TRPM4 expression. By use of these methods, it will for example be possible to identify compounds that target transcription factors which are relevant for TRPM4 expression. Also, suitable ribozymes or antisense DNA molecules can be identified in this way.

A number of different screening methods to evaluate the effects of candidate compounds on gene expression or enzyme activity may be used. The methods of the invention make use of any suitable method to detect a decrease in the expression level of the TRPM4 ion channel gene and/or in the activity of the TRPM4 ion channel. Suitable methods include e.g. biochemical or cellular methods. The skilled person would be able to identify such methods with his or her common knowledge.

For example, a decrease in the expression level of the TRPM4 ion channel gene may be detected by methods which allow the quantification of the transcription or the translation product of the TRPM4 ion channel gene, e.g. the quantification of TRPM4 mRNA or protein. Such methods are well known in the art. For example, polymerase chain reaction (PCR)-based methods, such as standard PCR, real-time PCR and quantitative real-time PCR, or Northern Blots may be used to determine the concentration of the TRPM4 mRNA. The concentration will be determined relative to a sample which is not contacted with the respective candidate compound, i.e. relative to a negative control, or to the same sample before contacting it with the respective compound. The concentration of TRPM4 protein may analogously be determined with standard methods such as SDS-PAGE, enzyme linked immunosorbent assays (ELISA), Western Blots, mass spectrometry or any other suitable means. The TRPM4 protein concentration will then be compared to a sample which has not been contacted with the respective compound or to the same sample before contacting it with the respective compound.

The cell that expresses the functional TRPM4 ion channel is preferably a mammalian cell, more preferably a human cell. The cell can be derived from a cell line, preferably a neuron- or brain cell-derived cell line, or from a primary cell culture, more preferably from a primary neuronal cell culture.

The in vitro methods of the present invention may preferably be carried out as high throughput screening techniques which allow for the examination of thousands of different compounds in a short period of time. Candidate compounds for use in screening methods can be provided in the form of libraries which comprise a high number of synthetic or natural compounds. High throughput screening techniques are described in detail in the prior art. The compounds identified by the screening methods may be validated in animal models, such as mouse models to confirm their activity in vivo.

The candidate compounds used in the screening methods of the present invention can include all different types of molecules as described for the compounds of the present invention above.

The TRPM4 that is used in the above assays can be recombinantly expressed. Accordingly, it will be understood by the skilled person that the above assays can be performed not only with the specific sequences depicted in SEQ ID NO:1 and 2, but also with variants, derivatives and enzymatically active fragments of these TRPM4 sequences. As used herein, variants of TRPM4 are polypeptides that differ by one or more amino acid exchanges from the amino acid sequence shown in SEQ ID NO:1 or 2. Generally, any amino acid residue of the amino acid sequence shown in SEQ ID NO:1 or 2 can be exchanged for a different amino acid, provided the resultant sequence of the variant is still capable of forming a functional ion channel. In particular, variants for which a total of up to 5%, 10%, 15%, or 20% of the amino acids differs from the amino acid sequence shown in SEQ ID NO:1 or 2 are included. Polypeptides in which one or more amino acids were inserted in the amino acid sequence of SEQ ID NO:1 or 2 are also included as variants. Such insertions can be made at any position of the polypeptide shown in SEQ ID NO:1 or 2. Moreover, polypeptides in which one or more amino acids are missing in comparison with SEQ ID NO:1 or 2 are also considered to be variants of the polypeptides of SEQ ID NO:1 or 2. Such deletions can apply to any amino acid position of the sequence of SEQ ID NO:1 or 2.

Variants of TRPM4 will preferably have at least 80% sequence identity, more preferably at least 85% sequence identity, and even more preferably at least 90% sequence identity, e.g. 91%, 92%, 93%, 94%, 95%, 96%, 97%, 98%, 99% sequence identity, with the human TRPM4 ion channel protein shown in SEQ ID NO:1 or 2 when these sequences are optimally arranged, e.g. with the computer program GAP or BESTFIT using the default gap method. Computer programs for determination of the amino acid identity are known to the skilled person.

Enzymatically active fragments of the sequence shown in SEQ ID NO:1 or 2 or variants thereof are to be understood to refer to peptides or polypeptides that differ from the amino acid sequence shown in SEQ ID NO:1 or 2 or from the above-defined variants thereof by the absence of one or more amino acids at the N-terminus and/or at the C-terminus of the peptide or polypeptide.

Derivatives of the polypeptides shown in SEQ ID NO:1 or 2 or of the variants thereof refer to polypeptides that possess amino acids with structural modifications, for example, modified amino acids, relative to a polypeptide shown in SEQ ID NO:1 or 2 or variants thereof. These modified amino acids can be, e.g. amino acids that have been altered by phosphorylation, glycosylation, acetylation, thiolation, branching and/or cyclization. It is preferred that the variants or derivatives of the TRPM4 polypeptide shown in SEQ ID NO:1 or 2 or the active fragments of this polypeptide or its variants retain at least 75%, and preferably up to 80%, 85%, 90% or even up to 99% of the ion channel activity of the TRPM4 polypeptide shown in SEQ ID NO:1 or 2.

In another aspect, the invention relates to the use of: (a) a polypeptide comprising the amino acid sequence shown in SEQ ID NO:1 or SEQ ID NO:2 or a variant thereof having at least 80%, more preferably at least 90% sequence identity to the amino acid sequence shown in SEQ ID NO:1 or SEQ ID NO:2; or (b) a polynucleotide encoding a polypeptide of (a) or the complement thereof for identifying pharmaceutically active compounds for treating or preventing an inflammatory, neurodegenerative disease. The neurodegenerative disease is preferably a disease that is associated with glutamate excitotoxicity. More preferably, it is selected from the group consisting of MS, Parkinson's disease, Alzheimer's disease, and amyotrophic lateral sclerosis, wherein MS is particularly preferred.

Example 1: TRPM4 Deficiency Ameliorates Experimental Autoimmune Encephalomyelitis (EAE)

In order to investigate whether TRPM4 modulates the pathogenesis of EAE, knockout mice with a dysfunctional Trpm4 gene (Trpm4$^{-/-}$) and wild-type (WT) mice were immunized with the myelin oligodendrocyte glycoprotein peptide 35–55 (MOG$_{35-55}$) in order to induce EAE in these animals. The sequence of the MOG35–55 peptide used for immunization is shown in SEQ ID NO:3. Briefly, C57BL/6 Trpm4$^{-/-}$ mice (Vennekens et al. (2007), *Nat Immunol.* 8:312-320) and Trpm4$^{+/+}$ littermates (referred to as WT controls) were immunized subcutaneously with 200 μg/mouse MOG$_{35-55}$ in complete Freund's adjuvant (Sigma-Aldrich) containing 4 mg/ml Mycobacterium tuberculosis (H37Ra, Difco). In addition, 200 ng pertussis toxin (Calbiochem) was injected intravenously on the day of immunization and 48 h later. The mice were sex and age (6-10 weeks) matched and were scored for clinical signs every day over a period of 60 days by the following system: 0, no clinical deficits; 1, tail weakness; 2, hind limb paresis; 3, partial hind limb paralysis; 3.5, full hind limb paralysis; 4, full hind limb paralysis and fore limb paresis; 5, pre-morbid or dead. Animals were sacrificed when their scores reached 4 or higher. Clinical scores (FIG. 1a) and body weight changes (FIG. 1b) were determined in triplicate for groups of WT EAE (n=15) and Trpm4$^{-/-}$ EAE (n=10) mice after immunization.

Results: As can be taken from FIG. 1, TRPM4 deficiency resulted in an overall reduced disease severity (P<0.01; FIG. 1a) and a significantly better recovery from weight loss (P<0.01; FIG. 1b) compared with WT littermates during EAE. These results indicate a decisive role of TRPM4 in mediating clinical disability in EAE.

Example 2: Analysis of Immune Cell Activation by Detecting Incorporation of [methyl-$^3$H]-thymidine Since EAE is an autoimmune disease and TRPM4 was previously shown to fulfill functions in immune cell activation and migration, it was first examined whether the protective phenotype in Trpm4$^{-/-}$ could be explained by altered immune cell activation or infiltration. For this purpose, C57BL/6 Trpm4$^{-/-}$ mice and WT controls were treated as described in Example 1. For assessing T-cell proliferation, single cell suspensions from draining lymph nodes and spleens were prepared 15 days after immunization from WT EAE (n=6) and Trpm4$^{-/-}$ EAE (n=6) mice by homogenizing the tissues through a 40 μm cell strainer (BD Biosciences). Cells were sedimented by centrifugation (300×g, 7 min, 4° C.) and splenic red blood cells were lysed in red blood cell lysis buffer for 7 min at 4° C. Cells were washed once in PBS and resuspended in buffer. The lymph node cells obtained from the immunized animals were cultured in 96-well plates (Sarstedt) at 2×10$^5$ cells/well in mouse complete medium and re-stimulated with different concentrations of the MOG$_{35-55}$ peptide or anti-CD3 (145-2C11, eBioscience). T cell proliferation was assessed by incorporation of [methyl-$^3$H]-thymidine as follows: After 2 days, cells were pulsed with 1 μCi [methyl-$^3$H]-thymidine (Amersham) per well for 16 h. Cells were harvested and spotted on filtermats with a Harvester 96 MACH III M (Tomtec) according to manufacturer's instructions. Incorporated activity per 96-well was assessed in a beta counter (1450 Microbeta, Perkin-Elmer) in counts per minute (cpm). The stimulation index of the applied peptides or antibodies was calculated by dividing the mean incorporated activity of stimulated wells by the mean of unstimulated control wells.

Figure 2:
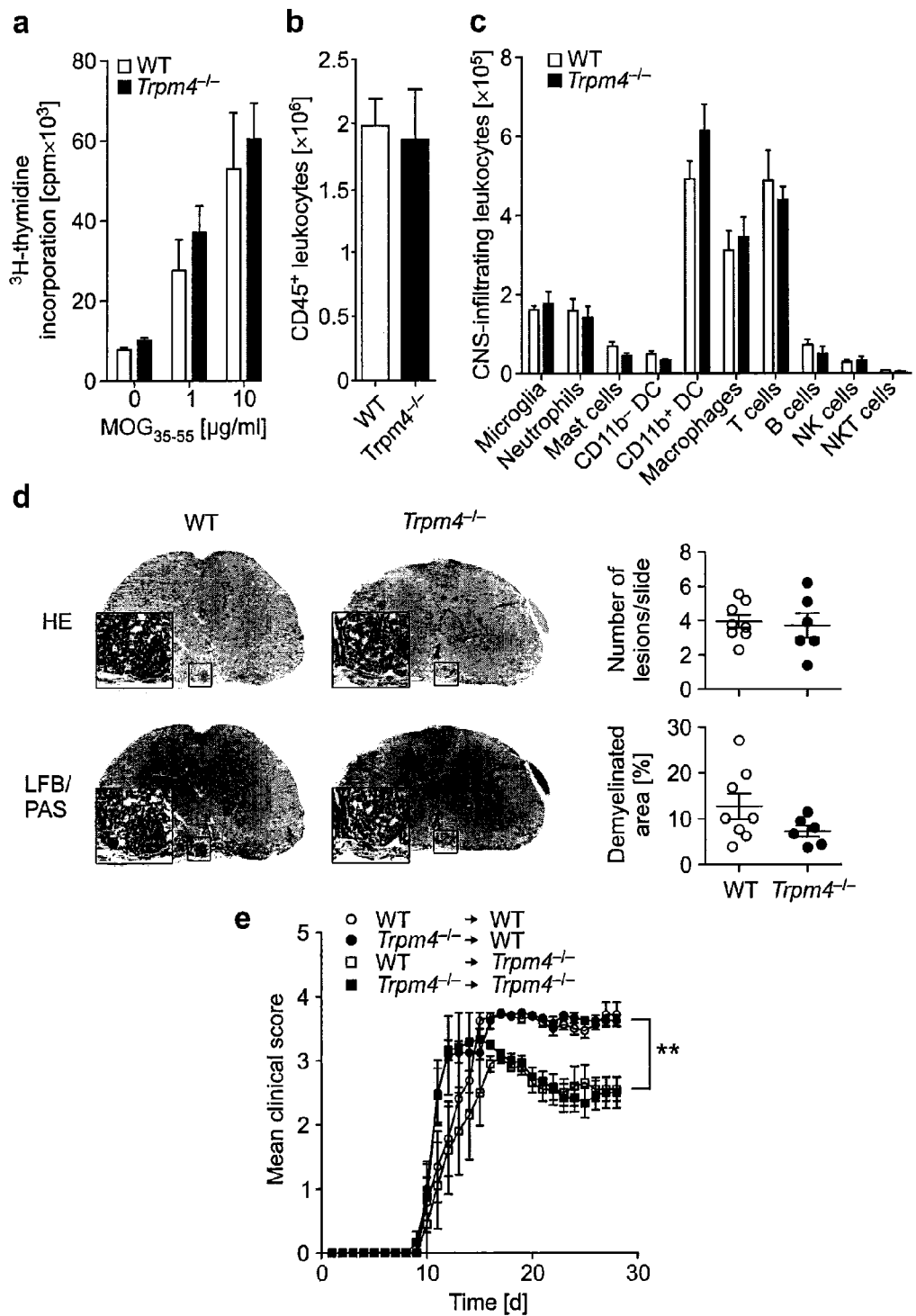
FIG. 2 demonstrates that Trpm4$^{-/-}$ mice show no EAE-relevant immune system alterations. (a) T cell proliferation after re-stimulation in single cell suspensions of draining lymph nodes from WT EAE (n=6) and Trpm4$^{-/-}$ EAE (n=6) mice as assessed by incorporation of [methyl-$^3$H]-thymidin-infiltrating cells after immunization in WT EAE (n=4) and Trpm4$^{-/-}$ EAE (n=3) mice: (b) total number of isolated CD45$^+$ leukocytes; (c) CNS-infiltrating leukocyte subsets. In a, b and c, data are shown as mean values±s.e.m. of one representative experiment out of four. (d) Representative stainings and quantifications of spinal cord sections of diseased animals 21 days post immunization (n=8 for WT and n=5 for Trpm4$^{-/-}$) for cellular infiltration (HE) and myelin (LFB/PAS) to determine the amount of lesions and the extent of demyelination. (e) Clinical deficits in lethally irradiated WT and Trpm4$^{-/-}$ mice which received bone marrow transplantations from either genotype (WT in Trpm4$^{-/-}$, n=5; Trpm4$^{-/-}$ in Trpm4$^{-/-}$, n=6; WT in WT, n=8; Trpm4$^{-/-}$ in WT, n=6).

Results: The results of the [methyl-$^3$H]-thymidine incorporation studies are shown in FIG. 2a. It can be seen there that Trpm4$^{-/-}$ mice show no EAE-relevant immune system alterations. Evidently, the deletion of the gene Trpm4 did not alter the proliferation of peripheral T cells being specific for MOG$_{35-55}$ as analyzed by $^3$H-thymidine incorporation after MOG$_{35-55}$ immunization.

Example 3: Analysis of CNS Infiltrates by Flow Cytometry

Since the protective phenotype observed in Example 1 could not be explained by altered immune cell activation, CNS (brain and spinal cord) infiltrates were analyzed by flow cytometry. For the isolation of CNS-infiltrating immune cells, WT EAE (n=4) and Trpm4$^{-/-}$ EAE (n=3) mice were sacrificed by CO$_2$ inhalation and immediately transcardially perfused with ice-cold PBS. Brain and spinal cord were removed, minced with blades and digested in collagenase/DNAseI solution (Roche) for 45 min at 37° C. Tissue was triturated through a 40 μm cell strainer. The homogenized tissue was washed in PBS (300×g, 10 min, and 4° C.). Immune cells including microglia were separated from myelin, other glia and neuronal cells by centrifugation over a discontinuous percoll (GE Healthcare) gradient. The homogenized tissue was resuspended in 30% isotonic percoll, transferred into a 15 ml Falcon tube and 78% isotonic percoll was layered underneath. The gradient was centrifuged (1500×g, 30 min, 4° C.) and CNS-infiltrating immune cells were then recovered from the gradient interphase. The isolated cell fraction was washed two times in PBS and subsequently resuspended in buffer. The total number of isolated CD45$^+$ leukocytes was quantified using Tru-COUNT® beads (BD Bio-sciences). CNS-infiltrating leukocyte subsets were identified as CD45$^{int}$CD11b$^+$ microglia, CD45$^{high}$NK1.1$^+$CD3$^-$NK cells, CD45$^{high}$NK1.1$^+$CD3$^+$ NKT cells, CD45$^{high}$Ly$^-$6G$^+$ neutrophils, CD45$^{high}$CD11b$^-$c-Kit$^+$ mast cells, CD45$^{high}$Ly-6G-CD11b+CD11c− macrophages, CD45$^{high}$Ly-6G-CD11b−CD11c$^+$ DC, CD45$^{high}$Ly-6G-CD11b−CD11c−CD3$^+$ T cells and CD45$^{high}$Ly-6G-CD11b−CD11c−CD45R$^+$ B cells (all antibodies are rat IgG except for CD3 and CD11c (hamster IgG) and NK1.1 (mouse IgG), all from eBioscience except of c-Kit which was from Biolegend).

Results: Equal total numbers of CNS-infiltrating CD45$^+$ leukocytes (FIG. 2b) and the same subset composition of infiltrates were found in Trpm4$^{-/-}$ and WT mice (FIG. 2c). Of note, recruitment of dendritic cells and mast cells to the CNS was not influenced by Trpm4 deletion (data not shown). Further, numbers of FoxP3$^+$ regulatory or effector T cells, expression of the activation markers CD25 and CD69 as well as interferon-γ (IFN-γ), interleukin (IL)-17A, IL-4 and IL-10 cytokine production by CD4$^+$ T cells were not significantly altered in the periphery (spleen and lymph nodes) or CNS. Consequently, no significant difference with regard to the numbers of inflammatory lesions (HE) and extend of demyelination (LFB/PAS) (FIG. 2d) as well as densities of infiltrates with T cells (CD3) and macrophages/microglia (Mac3) were observed within spinal cords at day 21 post immunization, a time point at which the earliest significant differences in clinical disability between Trpm4$^{-/-}$ and WT mice are observed. Also, no difference in blood-brain-barrier integrity or serum glucose levels between Trpm4$^{-/-}$ EAE and WT EAE mice could be detected (data not shown).

Example 4: Bone Marrow Chimeric Mice

Finally, bone marrow (BM) chimeric mice were established by reconstituting lethally irradiated Trpm4$^{-/-}$ or WT mice with bone marrow from either Trpm4$^{-/-}$ or WT mice. This was followed by an active EAE induction in these chimeras. Bone marrow chimeric mice were generated by lethal whole-body irradiation (9 Gy; 1 Gy/min) using a caesium-137 gamma irradiator (BIOBEAM 2000) of 5-6-week-old recipient WT and Trpm4$^{-/-}$ mice which were reconstituted 24 h later with 5×10$^6$ bone marrow cells derived from tibiae and femurs from respective donors. The lethally irradiated mice received bone marrow transplantations from either genotype (WT into Trpm4$^{-/-}$, n=5; Trpm4$^{-/-}$ into Trpm4$^{-/-}$, n=6; WT into WT, n=8; Trpm4$^{-/-}$ into WT, n=6). In addition to WT and Trpm4$^{-/-}$ cells, BM cells from CD45 congenic C57BL/6 Ly5.1 mice (CD45.1) were transferred into irradiated C57BL/6 WT mice (CD45.2) and assessed reconstitution (>95%) by FACS analysis of peripheral blood cells of mice 6 weeks after grafting. After recovery of the recipients for 6 weeks, mice were actively immunized with MOG$_{35-55}$ to induce EAE. The recipient mice were scored for their clinical deficits.

Results: The results of the reconstitution experiments are depicted in FIG. 2e. The figure shows the results from the EAE experiments as mean values and statistical analyses were performed by two-way ANOVA; asterisks indicate statistical significance of Trpm4$^{-/-}$ in WT vs. WT in Trpm4$^{-/-}$; **P<0.01; other not shown significances are: Trpm4$^{-/-}$ in WT vs. Trpm4$^{-/-}$ in Trpm4$^{-/-}$, P<0.05; WT in WT vs. WT in Trpm4$^{-/-}$, P<0.01; WT in WT vs. Trpm4$^{-/-}$ in Trpm4$^{-/-}$, P<0.05; Trpm4$^{-/-}$ in Trpm4$^{-/-}$ vs. WT in Trpm4$^{-/-}$, n.s.; WT in WT vs. Trpm4$^{-/-}$ in WT, n.s.; results from one representative experiment out of two are shown. It can be seen that Trpm4 deletion in donor BM did not affect the disease course. Protection from disease was only observed in mice that received the Trpm4$^{-/-}$ BM, but not in mice that received WT BM (P<0.01).

Taking together the results from Examples 2-4, it is evident that the absence of TRPM4 does not impair the activation or recruitment of disease-relevant immune cells during autoimmune inflammation of the CNS. It is therefore to be concluded that TRPM4 signaling within the CNS parenchyma is responsible for the altered disease course in Trpm4$^{-/-}$ mice.

Example 5: TRPM4 Expression in Neurons and Axons

In order to understand the contribution of TRPM4 to the ameliorated EAE course, TRPM4 expression in the CNS of humans and mice was analyzed.

a) Preparation and Analysis of Murine Tissues

Mice were anesthetized with an intraperitoneal injection of 100 μl per 10 g of body weight of a mixture of 10 mg/ml esketamine hydrochloride (Pfizer), 1.6 mg/ml xylazine hydrochloride (Bayer) and water. Afterwards the animals were perfused with 0.1 M phosphate buffer and fixed with 4% paraformaldehyde (PFA) in 0.1 M phosphate buffer. The spinal cords were resected and fixed for 30 min with 4% PFA and cryoprotected in 30% sucrose in PBS at 4° C. Midcervical spinal cord sections were cut transversely at 12 μm with a freezing microtome (Leica Jung CM3000) and stored in a cryoprotective medium (Jung) at −80° C. For immunohistochemistry the sections were incubated in blocking solution (5% normal donkey serum in PBS) containing 0.1% Triton X-100 at room temperature for 45 min and subsequently stained simultaneously or consecutively overnight at 4° C. with antibodies against the following structures: Phosphorylated neurofilaments (SMI 31, mouse IgG, 1:1,000; Covance), non-phosphorylated neurofilaments (SMI 32, mouse IgG, 1:1,000; Covance), neuronal nuclei (NeuN, mouse IgG, 1:200, Millipore) or TRPM4 (rabbit IgG, 1:100, Abcam). Secondary antibodies were Alexa Fluor 488—coupled donkey antibodies recognizing rabbit IgG, Cy3-coupled goat antibodies recognizing mouse IgG and Alexa Fluor 488-coupled goat antibodies recognizing mouse IgG (all 1:600, Dianova). DNA was stained with Hoechst 33258 (Invitrogen). Control experiments with no primary or secondary antibodies showed no staining (data not shown). Analyses of the sections were done with a Leica TCS SP2 confocal microscope. For quantification of axonal loss multiple representative images were taken with a 63-fold lens from the corticospinal tract and the dorsal column and axons were counted with ImageJ software based on a minimum diameter of 6.15 μm$^2$. Threshold intensities were fixed across experimental groups for each type of tissue examined. Accuracy of automated counting technique was confirmed by manual counting of sample images. Neuronal somata of the gray matter were counted manually.

b) Preparation and Analysis of Human Tissue

Histopathological analysis of MS tissue was performed on PFA-fixed sections from human brain biopsies of patients with MS. All tissue blocks were first classified with regard to lesional activity. Avidin-biotin technique with 3,3-diaminobenzidine was used for the visualization of bound primary antibodies. For fluorescence immunohistochemistry, MS biopsies were consecutively incubated with antibodies recognizing antigens in axons (neurofilament, mouse IgG1, Clone 2F11, Dako). Bound antibodies were visualized with species and immunoglobulin subtype specific secondary antibodies (Cy2 anti-mouse IgG from Jackson ImmunoResearch and Alexa555 anti-mouse IgG1 from Invitrogen). Counterstaining of cells was performed with DAPI (Invitrogen).

c) Quantitative Real-Time PCR

Whole brain homogenates and cultured primary neurons after 4 weeks of culture (see below Example 7) of WT and Trpm4$^{-/-}$ mice were analyzed by quantitative Real-Time PCR for TRMP4 expression. RNA was purified by TRIzol Reagent (Invitrogen) and cDNA synthesis was performed with RevertAid H Minus First Strand cDNA Synthesis Kit (Fermentas) according to the manufacturers' protocols. For quantitative Real-Time PCRTaqMan Gene Expression Assays Mm00613159_m1 (Trpm4) and Mm99999915_g1 (Gapdh) were used with a 7900HT Fast Real-Time PCR System (all Applied Biosystems). ACT values were calibrated to whole brain cDNA of WT mice.

Figures 3A, 3B:
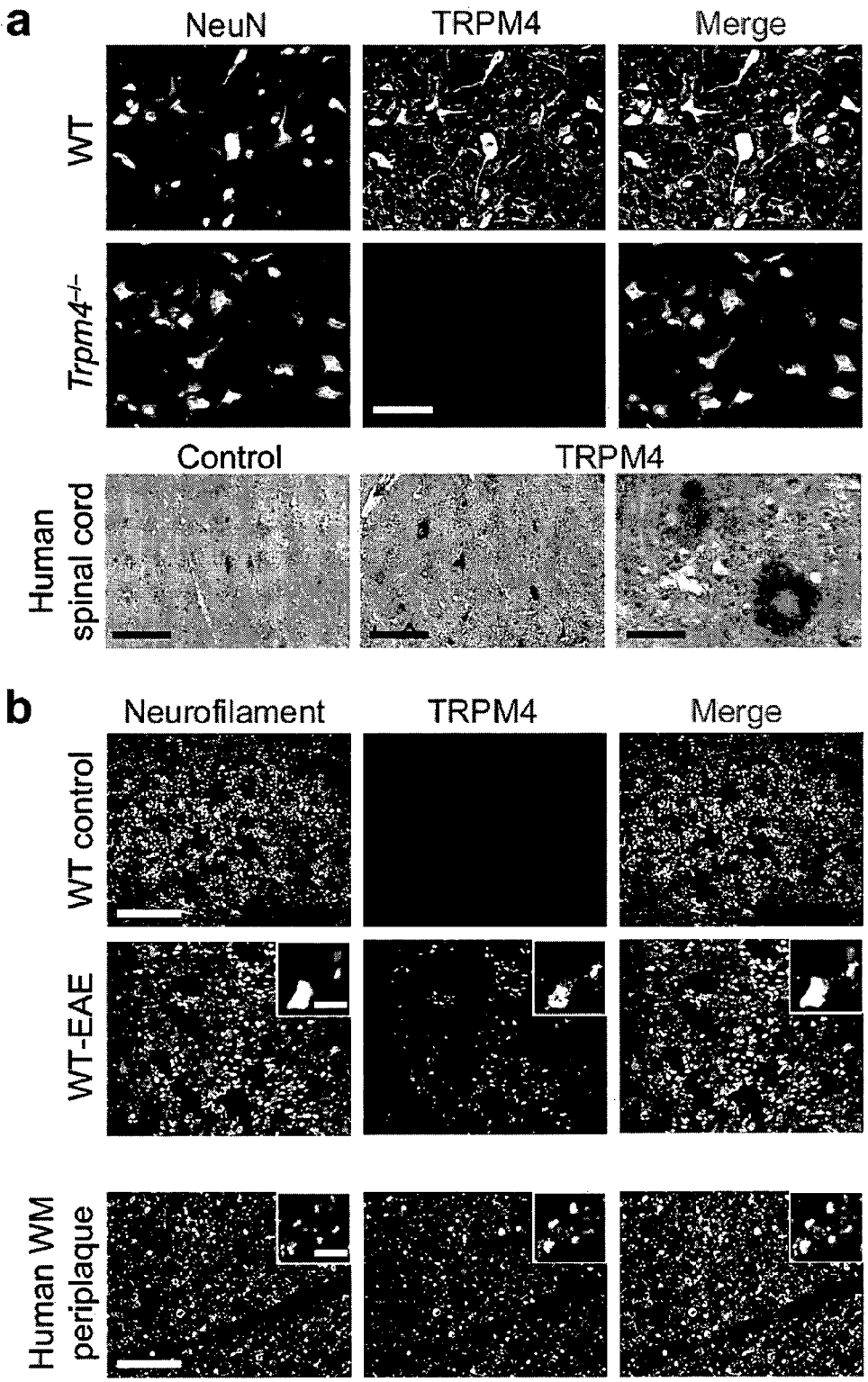
FIGS. 3A and 3B shows that TRPM4 is neuronally expressed in mice and humans. (a) co-localization of TRPM4 and neuronal nuclei (NeuN) in cervical spinal cord sections of healthy WT and Trpm4$^{-/-}$ mice and immunohistochemical stainings of TRPM4 as well as control staining in human spinal cord sections. (b) co-localizations between TRPM4 and phosphorylated and non-phosphorylated neurofilament H (SMI 31 and SMI 32) in cervical spinal cord sections of healthy WT and in acutely inflamed lesions of WT-EAE mice as well as TRPM4 and neurofilaments in periplaque white matter lesions of MS patients.
Figure 3C:
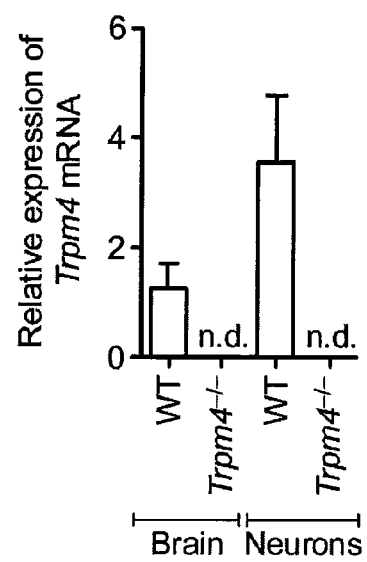
FIG. 3C shows Quantitative real-time PCR of Trpm4 transcripts from WT and Trpm4–/– whole brain homogenates and E16 hippocampal neurons after 4 weeks of culture.

Results: Trpm4 mRNA was detected by quantitative real-time PCR of Trpm4 of transcripts from WT and Trpm4$^{-/-}$ whole brain homogenates and compared with the Trpm4 mRNA in E16 hippocampal neurons after 4 weeks of culture (FIG. 3c). An increased number of transcripts was found in cultured hippocampal neurons (FIG. 3c), while no signal was detectable in Trpm4-deficient neurons. In addition, TRPM4 expression was recorded by immunohistochemistry in spinal cord motor neurons in WT, but not in Trpm4$^{-/-}$ mice (representative immunohistochemical stainings are depicted in FIG. 3a). Similarly, motor neurons of spinal cord autopsy from human patients with MS were labeled by immunohistochemistry with an antibody against human TRPM4 (FIG. 3a).

FIG. 3b shows co-localizations between TRPM4 and phosphorylated and non-phosphorylated neurofilament H (SMI 31 and SMI 32) in cervical spinal cord sections of healthy WT (upper panels) and in acutely inflamed lesions of WT EAE mice (middle panels; day 14 post immunization; scale bars: 50 µm and inset 3 µm) as well as TRPM4 and neurofilaments in periplaque white matter lesions of MS patients (lower panels; scale bars: 50 µm and inset 12 µm). TRPM4 immunoreactivity was observed within axonal processes at the edge of EAE lesions in WT mice in contrast to axons of healthy WT animals and Trpm4$^{-/-}$ mice (representative immunohistochemical stainings in FIG. 3b, data for Trpm4$^{-/-}$ not shown). Equally, TRPM4-positive axons were identified in affected spinal cords of MS patients in the periplaque white matter (representative immunohistochemical stainings in FIG. 3b) and a substantial fraction of axons in the periplaque white matter of MS brain lesions as well as cortical neurons were labeled by TRPM4 antibodies (data not shown). However, no change was detected in TRPM4 expression in neuronal somata in the inflammatory vicinity in mice and humans (data not shown). Together these data provide evidence that TRPM4 is physiologically expressed within the neuronal coma and in a fraction of axons of diseased EAE mice and MS patients, which suggest a contribution of TRPM4 to inflammation-induced neuronal and axonal degeneration.

Example 6: Reduced Axonal/Neuronal Injury in Trpm4$^{-/-}$ Mice

Since TRPM4 expression patterns suggested an involvement in axonal and neuronal injury mechanisms, it was tested whether the observed ameliorated EAE phenotype of Trpm4$^{-/-}$ mice was reflected in axonal immunohistochemical studies. For this purpose, histopathological analysis of EAE tissue was performed on PFA-fixed cross-sections (8 to 10 per animal) of lumbar and thoracic spinal cords. Digital images of tissue sections were recorded at 200-fold magnification using Zeiss MIRAX MIDI Slide Scanner (Carl Zeiss, MicroImaging GmbH, Germany). Numbers of inflammatory foci per spinal cord cross sections were quantified on hematoxylin and eosin (HE) stained sections and the average of inflammatory foci per analyzed cross-sections are expressed as inflammatory index. The extent of demyelination was quantified by measuring the demyelinated area of LFB/PAS-stained sections using a Mirax Viewer (Carl Zeiss, MicroImaging GmbH, Germany). The area of demyelination was calculated as percentage of total analyzed area of white matter within a given section. Immunostaining for the amyloid precursor protein (APP, clone 22C11, Chemicon) was used as a marker of acute axonal damage. Mice were also stained for neurofilaments (SMI 31 and SMI 32) in the corticospinal tract and dorsal column and for neuronal nuclei (NeuN) in the gray matter of cervical spinal cord sections (FIG. 4b). Further immunostaining was performed to assess infiltrates of activated macrophages/microglia (MAC3, Clone M3/84, BP Pharmingen) and T cells (CD3, Clone CD3-12, AbDSerotec). Avidin-biotin technique with 3,3-diaminobenzidine was used for the visualization of bound primary antibodies. The average density of activated macrophages/microglia and T cells was analyzed automatically applying a custom-programmed script in Cognition Network Language based on the Definiens Cognition Network Technology® platform (Definiens Developer XD software). Briefly, the programmed script first discriminates between tissue and background (no tissue) by spectral difference detection. Subsequently, the area of detected tissue (region of interest, ROI) is calculated and immunostained cells (CD3 or Mac3, respectively) within this ROI are detected based on their dark brown color. To split cells that were localized in dense clusters into single cells, nuclei were detected based on their blue color in Hemalaun counterstaining. Only immunoreactive brown structures displaying a blue nucleus in the center were further classified as "cells". APP-positive axons within white matter spinal cord sections were measured using an ocular counting grid and expressed as APP$^+$ spheroids/mm$^2$.

Figure 4:
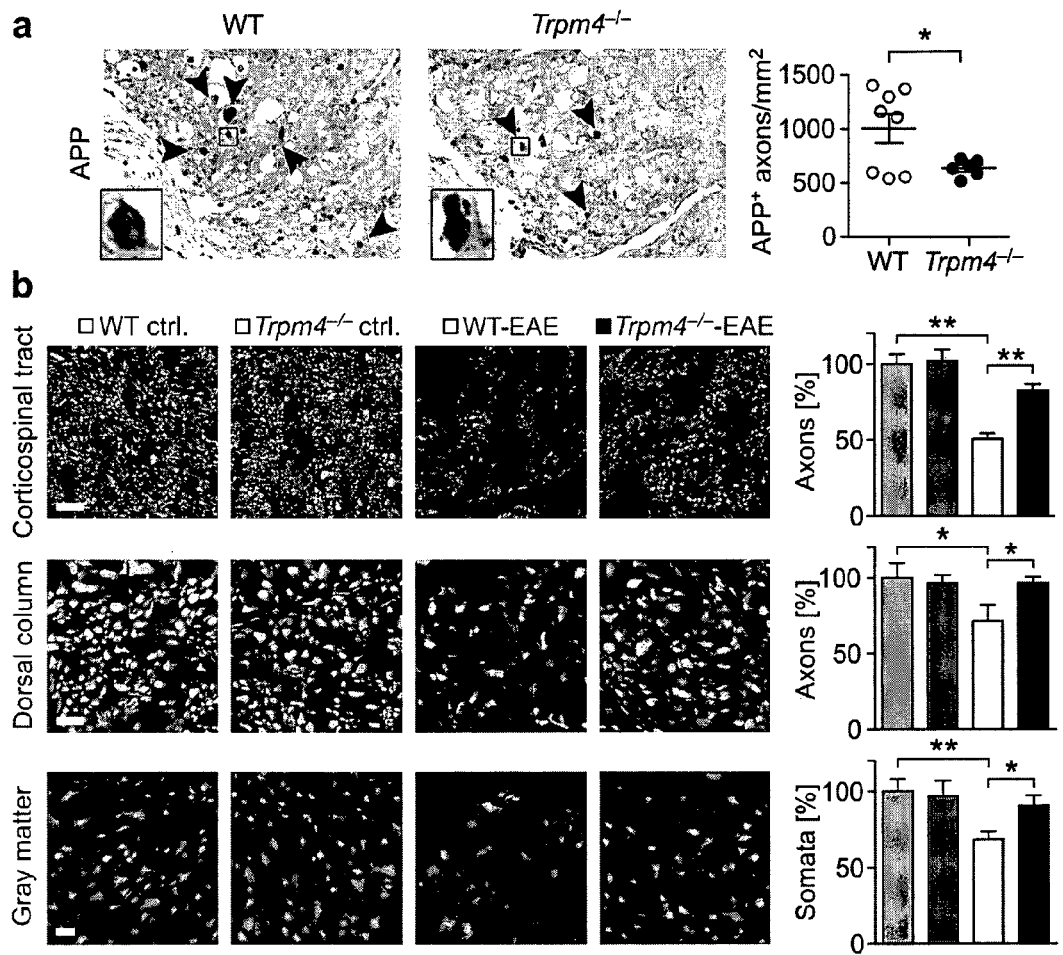
FIG. 4 depicts that Trpm4–/– mice show reduced axonal and neuronal loss during EAE. (a) Diseased WT and Trpm4–/– animals 21 days post immunization stained for amyloid precursor protein (APP). (b) WT-control, WT-EAE, Trpm4–/– control and Trpm4–/– EAE mice were stained for neurofilaments (SMI 31 and SMI 32) in the corticospinal tract and dorsal column and for neuronal nuclei (NeuN) in the gray matter of cervical spinal cord sections. Numbers of axons and somata were counted manually and by ImageJ software. Asterisks indicate statistical significance; *P<0.05, **P<0.01.

Results: Trpm4$^{-/-}$ mice showed reduced axonal and neuronal loss during EAE (FIG. 4). Indeed, fewer axonal spheroids were observed by immunostaining against amyloid precursor protein (APP), an acute injury marker for axons, within EAE lesions in Trpm4-deficient animals in comparison to WT animals at day 21 post immunization (dpi) (n=8 for WT and n=5 for Trpm4$^{-/-}$; P<0.05; FIG. 4a). Consequently, there was a marked preservation of axons in the corticospinal tract (P<0.01) and dorsal column (P<0.01) as well as of neuronal cell bodies in the gray matter of the spinal cord (P<0.05) of Trpm4$^{-/-}$-EAE mice in comparison to WT-EAE mice in immunohistochemical analyses at day 60 post immunization (representative images in FIG. 4b;

WT-control (n=4), WT EAE (60 dpi; n=10), Trpm4$^{-/-}$-control (n=4) and Trpm4$^{-/-}$ EAE (60 dpi; n=9); Scale bars: 10 μm (corticospinal tract and dorsal column) and 50 μm (gray matter)). These results indicate a profound resistance of axons and neurons in Trpm4$^{-/-}$ mice towards hostile inflammatory challenges leading to a neuro-axonal preservation and less clinical disability.

Example 7: Excitotoxic Cell Death is Driven by TRPM4-Dependent Inward Currents a) Resistance Towards Neurotoxic Challenges In Vitro It was tested whether the increased neuro-axonal preservation in Trpm4-deficient mice can be explained by a resistance towards ATP depletion and glutamate-mediated Ca$^{2+}$ influx in vitro. For this purpose, experiments were conducted with cells obtained from neuronal cell culture. Briefly, on day 16 after mating of Trpm4$^{+/-}$ mice, pregnant females were sacrificed by CO$_2$. The embryos were taken out and decapitated separately followed by dissection and dissociation of the hippocampus. In addition, a separate piece of tissue was taken for genotyping. Subsequently, the cells were plated at a density of 1×10$^5$ cells in 24-well plates with neurobasal medium supplemented with L-glutamine, B-27 and penicillin/streptomycin (all Invitrogen). Three days after culturing ARAC (Sigma-Aldrich) was added to avoid proliferation of glial cells.

Figure 5:
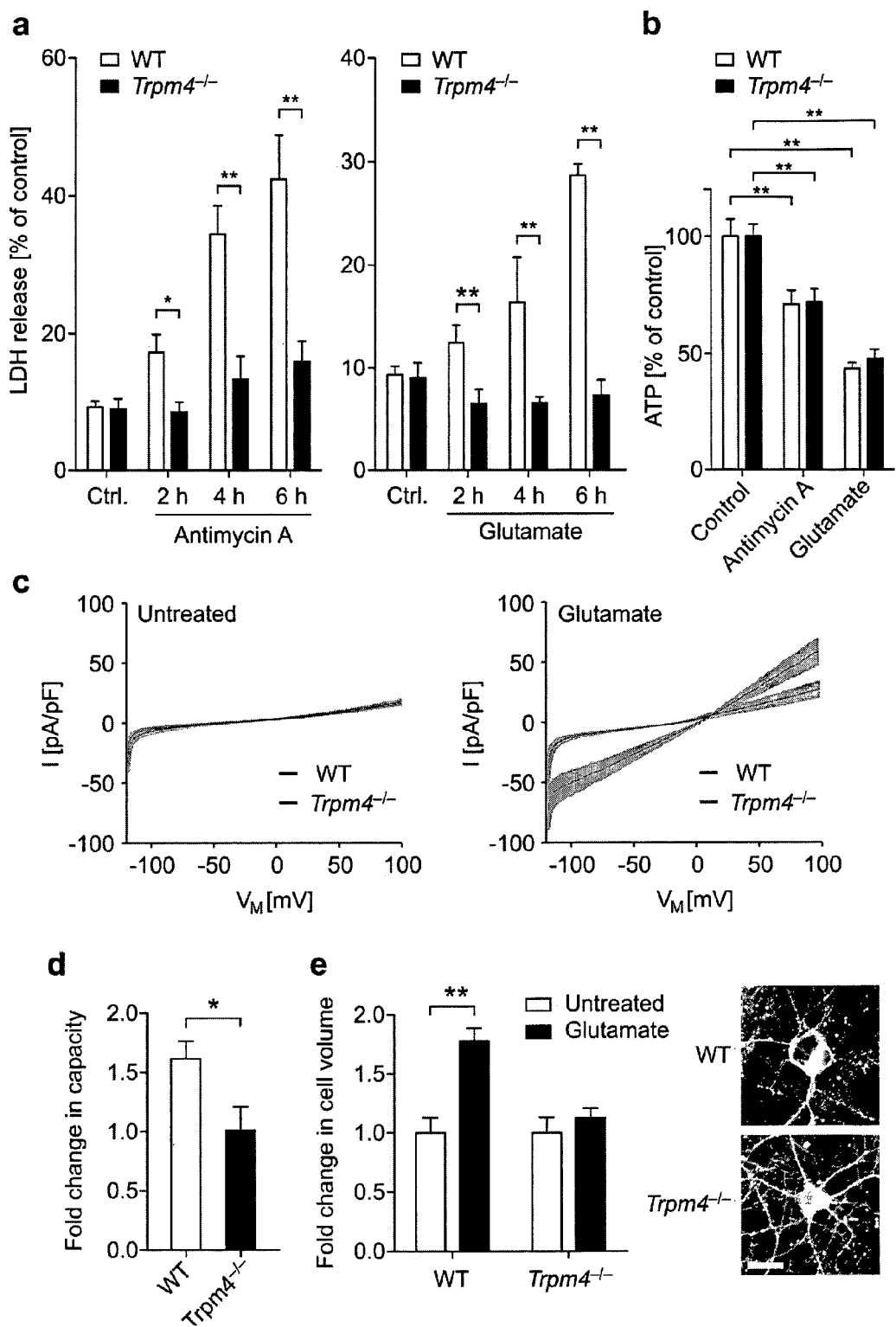
FIG. 5 shows that TRPM4 contributes to excitotoxic cell death in vitro. (a) Cell integrity of hippocampal neurons as measured by LDH concentrations in supernatant of untreated cells or cells treated with 0.5 μM antimycin A or 50 nM glutamate. (b) ATP levels of WT and Trpm4$^{-/-}$ hippocampal neurons after 4 h of antimycin A or glutamate administration. (c) Whole-cell patch-clamp recordings in hippocampal neurons of E16 embryos from WT and Trpm4$^{-/-}$ mice after 10 days in culture, under resting conditions (untreated) and after administration of 50 nM glutamate for 2 h. Normalized current-voltage relationship. (d) The fold change in membrane capacity after 50 nM glutamate incubation as compared to those of untreated controls of WT and Trpm4$^{-/-}$ neurons. (e) Hippocampal neurons of E16 embryos from WT and Trpm4$^{-/-}$ mice after 10 days in culture. Glutamate treated and control cells were stained for their cytoskeleton by β-tubulin III. Cell volumes were calculated. Representative pictures of neuronal cells from WT and Trpm4$^{-/-}$ mice after glutamate incubation for 2 h. Scale bar: 30 μm.

After 4 weeks of culture experimental challenges were added (FIG. 5a). To examine the cell integrity, LDH concentrations were measured in the supernatant according to the manufacturers' protocol (Roche) from untreated and stressed neurons by ELISA (VICTOR$^2$, Wallac) 2, 4 and 6 h after addition of 50 nM glutamate (Invitrogen), 300 μM H$_2$O$_2$ (Sigma-Aldrich) or 0.5 μM antimycin A (Sigma-Aldrich) (FIG. 5a). The percentages of damaged cells were calculated by setting 2% Triton X-100 treated cells as 100%. ATP levels of neuronal cells after treatment with either glutamate or antimycin A were quantified from cell lysates by using a luciferin based ATP determination kit (Molecular Probes) after 4 h of antimycin A or glutamate administration.

Immunocytochemistry of treated and control neurons was performed by fixing cells with 4% PFA for 30 min at room temperature and permeabilizing them with ice cold 80% methanol for 6 min. The cells were stained simultaneously or consecutively overnight at 4° C. with the following antibodies: TRPM4 (rabbit IgG, 1:100, Abcam) and β-tubulin III (mouse IgG, 1:500, Sigma-Aldrich). Secondary antibodies were Alexa Fluor 488—coupled donkey antibodies recognizing rabbit IgG, Cy3-coupled goat antibodies recognizing mouse IgG, Alexa Fluor 488—coupled donkey antibodies recognizing mouse IgG and Alexa Fluor 488—coupled goat antibodies recognizing mouse IgG (all 1:600, Dianova). Actin filaments were stained with Alexa Fluor 555—coupled phalloidin (Invitrogen) and DNA with Hoechst 33258 (Invitrogen). The cell volumes of untreated neuronal cells (10 days in culture) and the cell volumes of the cells which were treated with 50 nM glutamate for 2 h were assessed by staining the cytoskeleton with β-tubulin III and Alexa Fluor 488—coupled donkey anti-mouse antibodies. Z-stack images of whole neuronal cells were taken with a confocal laser-scanning microscope (Leica TCS SP2) with a defined step size. The cell bodies were rearranged with Imaris software (bitplane) and the complete volumes were calculated by ImageJ software.

Results: Treatment of cultured hippocampal neurons with ATP-depleting (antimycin A) and calcium-dependent excitotoxic (glutamate) stimuli resulted in a time-dependent loss of cell integrity of WT neuronal cells, as measured by LDH release into the supernatant, while cells from Trpm4$^{-/-}$ mice remained largely unaffected by both stimuli (2 h, P<0.05; 4 and 6 h, P<0.01 for antimycin A; 2, 4 and 6 h, P<0.01 for glutamate; FIG. 5a). Interestingly, glutamate treatment led to an even more profound reduction of cytosolic ATP levels than antimycin A (all P<0.01; FIG. 5b), while cytosolic ATP levels of WT and Trpm4$^{-/-}$ mice were comparable in all experimental conditions. Consistently, reduction of ATP by glucose deprivation resulted in a similar protection of Trpm4$^{-/-}$ neurons (6 h, P<0.01; data not shown).

b) Influence of Glutamate on TRPM4-Mediated Cation Currents

Since a marked resistance of Trpm4$^{-/-}$ neurons against glutamate-induced excitotoxicity was observed and additionally a substantial reduction of neuronal ATP levels was detected under these conditions, it was then examined whether neuronal TRPM4-mediated cation currents are activated by glutamate treatment. For this, whole-cell patch-clamp recordings were performed with an EPC9 patch-clamp amplifier (HEKA Elektronik) at a sampling rate of 20 kHz. Patch electrodes had a DC resistance between 2 and 4 MΩ when filled with intracellular solution for whole-cell patches. An Ag—AgCl wire was used as a reference electrode. Capacitance and access resistance were monitored continuously, and cell membrane capacitance values were used to calculate current densities. Bath solution was composed of 156 mM NaCl, 5 mM CaCl$_2$, 10 mM glucose, and 10 mM HEPES at pH 7.4. The pipette solution contained 156 mM CsCl, 1 mM MgCl$_2$, 10 mM EGTA and 10 mM HEPES at pH 7.2. Free Ca$^{2+}$ in the pipette solution was 7.4 μM by addition of CaCl$_2$. Holding potential was 0 mV, and current traces were elicited by voltage ramps for 250 ms from −120 to +100 mV. During all recordings, 100 nM TTX (Sigma-Aldrich) and 1 μM nifedipine (Sigma-Aldrich) were added to the bath solution.

Whole-cell patch-clamp recordings were performed on hippocampal neurons of E16 embryos from WT and Trpm4$^{-/-}$ mice after 10 days in culture under resting conditions (untreated) and after administration of 50 nM glutamate for 2 h. Normalized current-voltage relationship for WT (untreated, n=11; glutamate incubation, n=7) and Trpm4$^{-/-}$ (untreated, n=9; glutamate incubation, n=7) cells obtained from 250 ms voltage ramps measured in the whole-cell patch-clamp configuration from −120 to +100 mV are shown. Holding potential was 0 mV. In parallel, hippocampal neurons of E16 embryos from WT (n=7) and Trpm4$^{-/-}$ (n=7) mice were cultured for 10 days. Glutamate treated and control cells were stained for their cyto-skeleton by β-tubulin III. Z-stacks of whole neuronal cells were taken with a confocal laser-scanning microscope and cell volumes were calculated. Representative pictures of neuronal cells from WT and Trpm4$^{-/-}$ mice after glutamate incubation for 2 h are shown (FIG. 5d: Scale bar 30 μm).

Results: Under resting conditions no differences in current density between hippocampal neurons from Trpm4$^{-/-}$ and WT mice were detected by whole-cell patch-clamp recordings. Strikingly, however, after incubation of the cells with glutamate, WT neurons showed a strong TRPM4-dependent inward current at negative potentials which was absent in Trpm4$^{-/-}$ neurons (FIG. 5c). During electrophysiological measurements, an increased cell capacity of glutamate-treated WT neurons compared to untreated neurons was additionally detected, while this increase was absent in Trpm4$^{-/-}$ neurons (P<0.05; FIG. 5d). Since a gain in capacity can reflect an increase in cell volume, we analyzed the cell size of neurons from Trpm4$^{-/-}$ and WT mice under resting conditions and after glutamate treatment in immunofluorescent stainings of the cytoskeleton. In agreement with the observed gain in capacity, the cell volume of glutamate-treated WT neurons increased substantially compared to untreated WT neurons (P<0.01). By contrast, glutamate-treated Trpm4$^{-/-}$ neurons showed similar cell volumes in treated and untreated conditions (FIG. 5e).

Together, these results indicate that TRPM4 ion channels can exert neuronal injury in the context of energy deficiency and excitotoxic glutamate stimulation, and that TRPM4-mediated inward currents are substantially increased after this stimulation with subsequent oncotic cell swelling and neuronal cell death. As both conditions, ATP depletion due to mitochondrial dysfunction and substantially increased glutamate concentrations are abundant phenomena in EAE and MS lesions (Campbell et al. (2011), *Ann Neurol.* 69:481-492), it has to be concluded that a pathological activation of TRPM4 occurs in EAE and MS. The results further imply that a TRPM4-dependent excessive Na$^+$ overload eventually causes oncotic cell swelling and neuronal cell death.

Example 8: Glibenclamide Reduces EAE Severity by TRPM4 Inhibition

Having established a decisive role of TRPM4 for neuroaxonal degeneration under neuroinflammatory conditions, it was next examined whether pharmacological inhibition of TRPM4 after EAE induction is able to exert a neuroprotective effect in vivo. Glibenclamide, a well-tolerated, FDA-approved oral antidiabetic drug, has been reported to effectively inhibit TRPM4 (Damien et al. (2007), *Cardiovasc Res.* 73:531-538; Becerra et al. (2011), *Cardiovasc Res.* 91:677-684). The influence of this drug was tested in groups of WT-EAE and Trpm4$^{-/-}$-EAE mice. WT EAE and Trpm4$^{-/-}$ EAE mice were treated as described in Example 1 above to determine mean clinical disability scores. Pharmacological blockade of TRPM4 was achieved by daily administration of 10 μg glibenclamide or DMSO control by intraperitoneal injections after onset of first clinical symptoms (n=8 for Trpm4$^{-/-}$+glibenclamide; for all other groups n=6). 25 mg glibenclamide (Sigma-Aldrich) were solved in 5 ml dimethylsulfoxid (DMSO, AppliChem) every day, and 200 μl of this solution were diluted in 9.8 ml phosphate buffered saline (PBS). Treatment was started when first clinical symptoms occurred (day 8 after immunization with MOG$_{35-55}$). Mice received 100 μl of this solution or 2% DMSO in PBS as control. Due to the higher burden of daily injections, mice that were treated with glibenclamide or DMSO-control received only 2 mg/ml M tuberculosis and 100 ng pertussis toxin for EAE immunization. Healthy WT mice (WT control) and WT EAE mice treated either with glibenclamide or vehicle (n=4 per group) were stained 30 days post immunization for neurofilaments (SMI 31 and SMI 32) in the corticospinal tract and dorsal column and for neuronal nuclei (NeuN) in the gray matter of cervical spinal cord sections as described above. Numbers of axons and somata were counted by ImageJ software.

Figure 6:
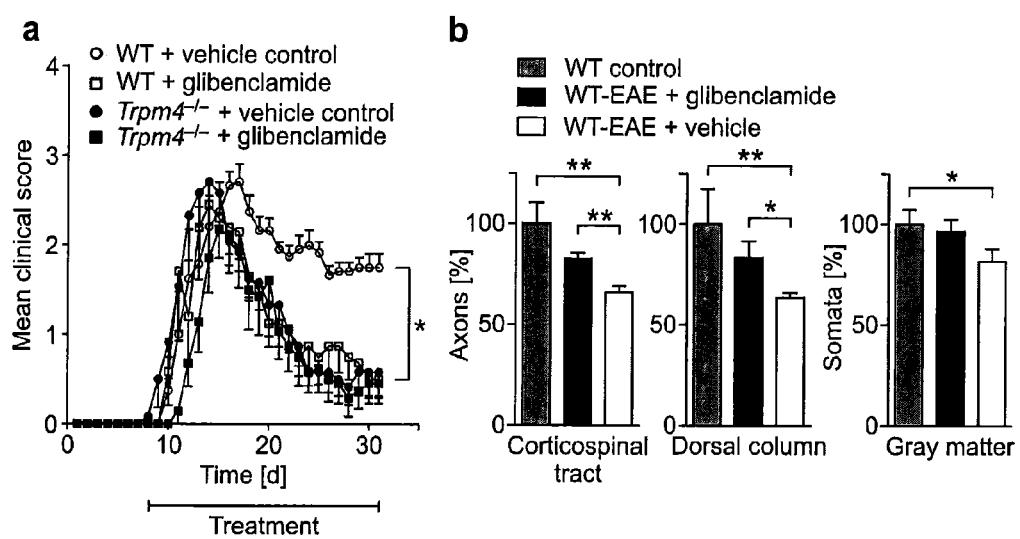
FIG. 6 shows that glibenclamide treatment reduces clinical disability and neurodegeneration in EAE mice. (a) Mean clinical disability scores for WT-EAE and Trpm4$^{-/-}$ EAE mice, which received daily injections of glibenclamide or DMSO control. Treatment was started when first clinical symptoms occurred (day 8 after immunization with MOG$_{35-55}$). (b) Healthy WT mice (WT control) and WT EAE mice treated either with glibenclamide or vehicle (n=4 per group) were stained 30 days post immunization for neurofilaments (SMI 31 and SMI 32) in the corticospinal tract and dorsal column and for neuronal nuclei (NeuN) in the gray matter of cervical spinal cord sections. Numbers of axons and somata were counted by ImageJ software.

Results: The results obtained from the glibenclamide study are shown in FIG. 6. Glibenclamide treatment reduces clinical disability and neurodegeneration in EAE mice. While glibenclamide ameliorated disability in WT EAE mice in comparison to vehicle control treated WT EAE animals (P<0.05), glibenclamide showed no additional clinical improvement in Trpm4$^{-/-}$ EAE mice, indicating that glibenclamide exerts its protective properties in EAE via targeting TRPM4. This was substantiated by a preservation of axons in the corticospinal tract (P<0.01) and dorsal column (P<0.05) of glibenclamide treated WT EAE mice in comparison to vehicle control treated WT EAE mice. Further, neuronal cell body loss in the gray matter of the spinal cord in WT EAE mice (P<0.05) was slightly diminished by glibenclamide treatment in comparison to vehicle control treated mice, although this preservation of neurons did not reach statistical significance (FIG. 6b).

The invention claimed is:

1. A method of treating multiple sclerosis in a subject in need of treatment thereof, the method comprising administering to the subject a therapeutically effective amount of glibenclamide or a pharmaceutically acceptable salt, solvate or tautomer thereof.

2. The method of claim 1, wherein the multiple sclerosis is relapsing remitting multiple sclerosis or secondary progressive multiple sclerosis.

3. The method of claim 2, wherein the glibenclamide is administered at a dose of between about 10 μg/kg to about 2000 μg/kg.

4. The method of claim 3, wherein the administration begins after the first clinical symptoms occur.

5. The method of claim 3, wherein the glibenclamide is administered once daily.

6. The method of claim 5, wherein the dose of glibenclamide is administered orally to the subject.

* * * * *